(12) United States Patent
Uozumi et al.

(10) Patent No.: US 11,192,965 B2
(45) Date of Patent: Dec. 7, 2021

(54) SOLID CATALYST COMPONENT FOR OLEFIN POLYMERIZATION, CATALYST FOR OLEFIN POLYMERIZATION, AND METHOD FOR PRODUCING OLEFIN POLYMER

(71) Applicant: TOHO TITANIUM CO., LTD., Chigasaki (JP)

(72) Inventors: Toshiya Uozumi, Chigasaki (JP); Hiroyuki Kono, Chigasaki (JP); Shinta Marui, Chigasaki (JP); Chika Uzawa, Chigasaki (JP)

(73) Assignee: TOHO TITANIUM CO., LTD., Chigasaki (JP)

( * ) Notice: Subject to any disclaimer, the term of this patent is extended or adjusted under 35 U.S.C. 154(b) by 817 days.

(21) Appl. No.: 16/070,105

(22) PCT Filed: Dec. 26, 2016

(86) PCT No.: PCT/JP2016/088680
§ 371 (c)(1),
(2) Date: Jul. 13, 2018

(87) PCT Pub. No.: WO2017/122521
PCT Pub. Date: Jul. 20, 2017

(65) Prior Publication Data
US 2021/0040247 A1    Feb. 11, 2021

(30) Foreign Application Priority Data
Jan. 14, 2016 (JP) .............................. JP2016-005186

(51) Int. Cl.
| | | |
|---|---|---|
| C08F 110/06 | (2006.01) | |
| C08F 4/659 | (2006.01) | |
| C08F 4/649 | (2006.01) | |
| C08F 4/654 | (2006.01) | |
| C08F 4/646 | (2006.01) | |
| C07C 69/618 | (2006.01) | |
| C07C 69/708 | (2006.01) | |

(52) U.S. Cl.
CPC .......... *C08F 110/06* (2013.01); *C07C 69/618* (2013.01); *C07C 69/708* (2013.01); *C08F 4/6465* (2013.01); *C08F 4/6492* (2013.01); *C08F 4/6494* (2013.01); *C08F 4/654* (2013.01); *C08F 4/65912* (2013.01)

(58) Field of Classification Search
CPC .. C08F 110/06; C08F 4/65912; C08F 4/6492; C08F 4/6494; C08F 4/654; C08F 4/6465; C07C 69/618; C07C 69/708
See application file for complete search history.

(56) References Cited

U.S. PATENT DOCUMENTS

| | | |
|---|---|---|
| 5,539,067 A | 7/1996 | Parodi et al. |
| 5,618,771 A | 4/1997 | Parodi et al. |
| 6,194,342 B1 | 2/2001 | Parodi et al. |
| 6,515,085 B1 | 2/2003 | Parodi et al. |
| 2016/0229935 A1 | 8/2016 | Wang et al. |
| 2016/0326277 A1 | 11/2016 | Sugano et al. |

FOREIGN PATENT DOCUMENTS

| | | |
|---|---|---|
| JP | 2014-201602 A | 10/2014 |
| WO | 2015/054951 A1 | 4/2015 |
| WO | 2015/107708 A1 | 7/2015 |

OTHER PUBLICATIONS

International Search Report dated Feb. 28, 2017, issued in counterpart International Application No. PCT/JP2016/088680 (2 pages).

*Primary Examiner* — Catherine S Branch
(74) *Attorney, Agent, or Firm* — Westerman, Hattori, Daniels & Adrian, LLP

(57) ABSTRACT

Provided is a solid catalyst component for olefin polymerization comprising an electron-donating compound other than a phthalate, the solid catalyst component being equal in the olefin-polymerizing activity and in the primary physical properties of the resulting polymer such as stereoregularity and molecular weight distribution to those with use of a phthalate as an electron-donating compound. A solid catalyst component for olefin polymerization comprises a magnesium atom, a titanium atom, a halogen atom, an ester compound (A) represented by a general formula (1) and a diester compound (B) represented by a general formula (2), wherein
a ratio represented by the following expression:

(content (mass %) of ester compound (A)/content (mass %) of diester compound (B))

is 0.05 to 50.

14 Claims, No Drawings

SOLID CATALYST COMPONENT FOR OLEFIN POLYMERIZATION, CATALYST FOR OLEFIN POLYMERIZATION, AND METHOD FOR PRODUCING OLEFIN POLYMER

TECHNICAL FIELD

The present invention relates to a solid catalyst component for olefin polymerization, a catalyst for olefin polymerization, and a method for producing an olefin polymer.

BACKGROUND ART

Conventionally, a solid catalyst including a catalyst component of a transition metal such as titanium and a catalyst component of a typical metal such as aluminum is widely known as a catalyst for olefin polymerization.

Conventionally, a solid catalyst component containing a magnesium atom, a titanium atom, a halogen atom and an electron-donating compound as essential components for use in polymerization of an olefin such as propylene is known. Also, many methods have been proposed to polymerize or co-polymerize olefins in the presence of a catalyst for olefin polymerization including the solid catalyst component, an organoaluminum compound and an organosilicon compound.

For example, in Patent Literature 1 (Japanese Patent Laid-Open No. 57-63310), a method for polymerizing propylene with use of a catalyst for olefin polymerization containing a solid titanium catalyst component with an electron-donating compound such as a phthalate supported, and an organoaluminum compound and an organosilicon compound having at least one Si—O—C bond as a promoter components, is proposed. In many literature including the patent literature described above, a method for obtaining a polymer with high stereoregularity under high polymerizing activity by using a phthalate as an electron-donating compound has been proposed.

However, di-n-butyl phthalate and benzyl butyl phthalate as one of phthalates are identified as substances of very high concern (SVHC) in Registration, Evaluation, Authorization and Restriction of Chemicals (REACH) regulation in Europe. From the viewpoint of reducing environmental impact, a demand for converting to a catalyst system without use of an SVHC substance is growing.

As an electron-donating compound that is not subject to SVHC regulation, a solid catalyst component made from a succinate, a maleate, a malonate, a diether or the like is known.

CITATION LIST

Patent Literature

[Patent Literature 1] Japanese Patent Laid-Open No. 57-63310

SUMMARY OF INVENTION

Technical Problem

A solid catalyst component with use of an electron-donating compound other than the phthalate described above, however, hardly provides performance equal to that of a solid catalyst component using a phthalate, and tends to be inferior in any one of the polymerizing activity in olefin polymerization and the primary physical properties of the resulting polymer such as stereoregularity and molecular weight distribution, so that further improvement is required.

Under these circumstances, an object of the present invention is to provide a solid catalyst component for olefin polymerization comprising an electron-donating compound other than a phthalate, the solid catalyst component being equal in the olefin-polymerizing activity and in the primary physical properties of the resulting polymer such as stereoregularity and molecular weight distribution to those with use of a phthalate as an electron-donating compound; a catalyst for olefin polymerization with use of the solid catalyst component for olefin polymerization; and a method for producing an olefin polymer.

Solution to Problem

Through extensive investigation to solve the technical problem described above, the present inventor has found that a solid catalyst component for olefin polymerization comprising a magnesium atom, a titanium atom, a halogen atom, a specific ester compound (A), and a specific diester compound (B), with a specific quantitative ratio of the content of the ester compound (A) to the content of the diester compound (B) can solve the technical problem. Based on the founding, the present invention has been accomplished.

In other words, the present invention provides:
(i) a solid catalyst component for olefin polymerization comprising a magnesium atom, a titanium atom, a halogen atom, an ester compound (A) represented by the following general formula (1):

$$R^1—O—C(=O)—CR^2R^3—CR^4R^5—O—R^6 \quad (1)$$

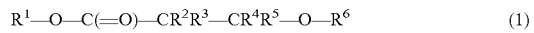

wherein $R^1$ and $R^6$ are each a hydrocarbon group having 1 to 24 carbon atoms and may be the same or different from each other, and $R^2$ to $R^5$ are each a hydrogen atom or a hydrocarbon group having 1 to 24 carbon atoms and may be the same or different from each other, and a diester compound (B) represented by the following general formula (2):

$$R^7R^8C=C(COOR^9)(COOR^{10}) \quad (2)$$

wherein $R^7$ and $R^8$ are each a hydrogen atom or a hydrocarbon group having 1 to 24 carbon atoms and may be the same or different from each other, and $R^9$ and $R^{10}$ are each a hydrocarbon group having 1 to 24 carbon atoms and may be the same or different from each other, wherein a ratio represented by the following expression:

(content (mass %) of ester compound (A)/content (mass %) of diester compound (B))

is 0.05 to 50.
(ii) the solid catalyst component for olefin polymerization according to the item (i), wherein at least one of the hydrocarbon groups having 1 to 24 carbon atoms constituting the $R^1$ to $R^{10}$ is a group selected from a linear alkyl group having 1 to 24 carbon atoms, a branched alkyl group having 3 to 24 carbon atoms, a vinyl group, a linear alkenyl group having 3 to 20 carbon atoms, a branched alkenyl group having 3 to 20 carbon atoms, a cycloalkyl group having 3 to 20 carbon atoms, a cycloalkenyl group having 3 to 20 carbon atoms, and an aromatic hydrocarbon group having 6 to 20 carbon atoms;
(iii) the solid catalyst component for olefin polymerization according to the item (i) or (ii), wherein at least one of the $R^3$ to $R^5$ is a hydrogen atom;

(iv) the solid catalyst component for olefin polymerization according to any one of the items (i) to (iii), wherein the $R^7$ is an aromatic hydrocarbon group;

(v) a catalyst for olefin polymerization comprising:
(I) the solid catalyst component for olefin polymerization according to any one of the items (i) to (iv);
(II) an organoaluminum compound represented by the following general formula (3):

$$R^{11}_p AlQ_{3-p} \qquad (3)$$

wherein $R^{11}$ is an alkyl group having 1 to 6 carbon atoms; Q is a hydrogen atom or a halogen atom; p is a real number satisfying $0 < p \leq 3$; if a plurality of $R^{11}$ are present, $R^{11}$ may be the same or different from each other; and if a plurality of Q are present, Q may be the same or different from each other; and
(III) an external electron-donating compound;
(vi) the catalyst for olefin polymerization according to the item (v), wherein the external electron-donating compound (III) is one or more selected from:
an organosilicon compound represented by the following general formula (4):

$$R^{12}_q Si(OR^{13})_{4-q} \qquad (4)$$

wherein $R^{12}$ is any of a linear alkyl group having 1 to 12 carbon atoms, a branched alkyl group having 3 to 12 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and q is an integer satisfying $0 \leq q \leq 3$, and if q is 2 or more, a plurality of $R^{12}$ may be the same or different from each other;

$R^{13}$ represents any of a linear alkyl group having 1 to 4 carbon atoms, a branched alkyl group having 3 to 4 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and a plurality of $R^{13}$ may be the same or different from each other; and
an organosilicon compound represented by the following general formula (5):

$$(R^{14}R^{15}N)_s SiR^{16}_{4-s} \qquad (5)$$

wherein $R^{14}$ and $R^{15}$ are any of a hydrogen atom, a linear alkyl group having 1 to 12 carbon atoms, a branched alkyl group having 3 to 12 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and $R^{14}$ and $R^{15}$ may be the same or different from each other and may be bonded to each other to form a ring;

$R^{16}$ is any of a linear alkyl group having 1 to 12 carbon atoms or a branched alkyl group having 3 to 12 carbon atoms, a vinyl group, an alkenyl group having 3 to 12 carbon atoms, a cycloalkyl group having 3 to 12 carbon atoms, an aromatic hydrocarbon group having 6 to 12 carbon atoms, a linear alkoxy group having 1 to 12 carbon atoms or a branched alkoxy group having 3 to 12 carbon atoms, a vinyloxy group, an allyloxy group having 3 to 12 carbon atoms, and an aryloxy group having 6 to 12 carbon atoms, and if a plurality of $R^{16}$ are present, each $R^{16}$ may be the same or different from each other, and s is an integer of 1 to 3;

(vii) the catalyst for olefin polymerization according to the item (v), wherein the external electron-donating compound (III) is a diether compound represented by the following general formula (6):

$$R^{17}R^{18}R^{19}COCH_2(R^{23}R^{24}C)CH_2OCR^{20}R^{21}R^{22} \qquad (6)$$

wherein $R^{17}$ to $R^{22}$ are any of a hydrogen atom, a linear alkyl group having 1 to 6 carbon atoms, a branched alkyl group having 3 to 6 carbon atoms, a cycloalkyl group having 3 to 6 carbon atoms, and a phenyl group, and may be the same or different from each other; and $R^{23}$ and $R^{24}$ are each any of a hydrogen atom, a linear alkyl group having 1 to 6 carbon atoms, a branched alkyl group having 3 to 6 carbon atoms, a cycloalkyl group having 3 to 6 carbon atoms, and a phenyl group, and may be the same or different from each other, and may also be bonded to each other to form a ring;
(viii) the catalyst for olefin polymerization according to the item (vi), wherein the organosilicon compound is one or more selected from phenyltrimethoxysilane, t-butylmethyldimethoxysilane, t-butylethyldimethoxysilane, diisopropyldimethoxysilane, isopropylisobutyldimethoxysilane, diisopentyldimethoxysilane, diphenyldimethoxysilane, dicyclopentyldimethoxysilane, cyclohexylmethyldimethoxysilane, tetramethoxysilane, tetraethoxysilane, t-butylmethylbis(ethylamino)silane, bis(ethylamino)dicyclohexylsilane, dicyclopentylbis(ethylamino)silane, bis(perhydroisoquinolino)dimethoxysilane, and diethylaminotriethoxysilane;
(ix) the catalyst for olefin polymerization according to the item (vii), wherein the diether compound is one or more selected from 2-isopropyl-2-isobutyl-1,3-dimethoxypropane, 2-isopropyl-2-isopentyl-1,3-dimethoxypropane, and 9,9-bis(methoxymethyl)fluorene; and
(x) a method for producing an olefin polymer comprising polymerizing an olefin in the presence of the catalyst for olefin polymerization according to any one of the items (v) to (ix).

Advantageous Effects of Invention

According to the present invention, a solid catalyst component for olefin polymerization comprising an electron-donating compound other than a phthalate, the solid catalyst component being equal in the olefin-polymerizing activity and in the primary physical properties of the resulting polymer such as stereoregularity and molecular weight distribution to those with use of a phthalate as an electron-donating compound; a catalyst for olefin polymerization with use of the solid catalyst component for olefin polymerization; and a method for producing an olefin polymer can be provided.

DESCRIPTION OF EMBODIMENTS

The solid catalyst component for olefin polymerization according to the present invention comprises a magnesium atom, a titanium atom, a halogen atom, an ester compound (A) represented by the following general formula (1):

$$R^1-O-C(=O)-CR^2R^3-CR^4R^5-O-R^6 \qquad (1)$$

wherein $R^1$ and $R^6$ are each a hydrocarbon group having 1 to 24 carbon atoms and may be the same or different from each other, and $R^2$ to $R^5$ are each a hydrogen atom or a hydrocarbon group having 1 to 24 carbon atoms and may be the same or different from each other, and a diester compound (B) represented by the following general formula (2):

$$R^7R^8C=C(COOR^9)(COOR^{10}) \qquad (2)$$

wherein $R^7$ and $R^8$ are each a hydrogen atom or a hydrocarbon group having 1 to 24 carbon atoms and may be the same or different from each other, and $R^9$ and $R^{10}$ are each a hydrocarbon group having 1 to 24 carbon atoms and may be the same or different from each other, wherein a ratio represented by the following expression:

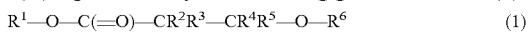
(content (mass %) of ester compound (A)/content (mass %) of diester compound (B))

is 0.05 to 50.

As the halogen atom contained in the solid catalyst component for olefin polymerization according to the present invention, for example, one or more selected from a fluorine atom, a chlorine atom, a bromine atom and a iodine atom are preferred, one or more selected from a chlorine atom, a bromine atom and a iodine atom are more preferred, and one or more selected form a chlorine atom and a iodine atom are furthermore preferred.

The solid catalyst component for olefin polymerization according to the present invention comprises an ester compound (A) represented by the following general formula (1):

$$R^1\text{—O—C}(\text{=O})\text{—CR}^2R^3\text{—CR}^4R^5\text{—O—}R^6 \quad (1)$$

wherein $R^1$ and $R^6$ are each a hydrocarbon group having 1 to 24 carbon atoms and may be the same or different from each other, and $R^2$ to $R^5$ are each a hydrogen atom or a hydrocarbon group having 1 to 24 carbon atoms and may be the same or different from each other.

In the ester compound (A) represented by the general formula (1), at least one of the hydrocarbon groups having 1 to 24 carbon atoms constituting the $R^1$ to $R^6$ is preferably a group selected from a linear alkyl group having 1 to 24 carbon atoms, a branched alkyl group having 3 to 24 carbon atoms, a vinyl group, a linear alkenyl group having 3 to 20 carbon atoms, a branched alkenyl group having 3 to 20 carbon atoms, a cycloalkyl group having 3 to 20 carbon atoms, a cycloalkenyl group having 3 to 20 carbon atoms, and an aromatic hydrocarbon group having 6 to 20 carbon atoms.

Examples of the linear alkyl group include any selected from ones having 1 to 24 carbon atoms, and one having 1 to 12 carbon atoms is preferred and one having 1 to 6 carbon atoms is more preferred.

Specific examples of the linear alkyl group include one or more selected from a methyl group, an ethyl group, a n-propyl group, a n-butyl group, a n-pentyl group, a n-hexyl group, a n-heptyl group, a n-octyl group, a n-nonyl group, a n-decyl group and the like.

Examples of the branched alkyl group include any selected from ones having 3 to 24 carbon atoms, and one having 3 to 12 carbon atoms is preferred and one having 3 to 6 carbon atoms is more preferred.

Specific examples of the branched alkyl group include one or more selected from alkyl groups having a secondary carbon atom or a tertiary carbon atom such as an isopropyl group, an isobutyl group, a t-butyl group, an isopentyl group and a neopentyl group.

Examples of the linear alkenyl group include any selected from ones having 3 to 20 carbon atoms, and one having 3 to 12 carbon atoms is preferred and one having 3 to 6 carbon atoms is more preferred.

Specific examples of the linear alkenyl group include one or more selected from a n-propenyl group, a n-butenyl group, a n-pentenyl group, a n-hexenyl group, a n-heptenyl group, a n-octenyl group, a n-nonenyl group, a n-decenyl group and the like.

Examples of the branched alkenyl group include any selected from ones having 3 to 20 carbon atoms, and one having 3 to 12 carbon atoms is preferred and one having 3 to 6 carbon atoms is more preferred.

Specific examples of the branched alkenyl group include one or more selected from alkenyl groups having a secondary carbon atom or a tertiary carbon atom such as an isopropenyl group, an isobutenyl group, a t-butenyl group, an isopentenyl group and a neopentenyl group.

Examples of the cycloalkyl group include any selected from ones having 3 to 20 carbon atoms, and one having 3 to 12 carbon atoms is preferred and one having 5 to 6 carbon atoms is more preferred.

Specific examples of the cycloalkyl group include one or more selected from a cyclopropyl group, a cyclobutyl group, a cyclopentyl group, a cyclohexyl group, a cycloheptyl group, a cyclooctyl group, a cyclononyl group, a cyclodecyl group and the like.

Examples of the cycloalkenyl group include any selected from ones having 3 to 20 carbon atoms, and one having 3 to 12 carbon atoms is preferred and one having 5 to 6 carbon atoms is more preferred.

Specific examples of the cycloalkenyl group include one or more selected from a cyclopropenyl group, a cyclobutenyl group, a cyclopentenyl group, a cyclohexenyl group, a cycloheptenyl group, a cyclooctenyl group, a cyclononenyl group, a cyclodecenyl group and the like.

Examples of the aromatic hydrocarbon group include any selected from ones having 6 to 20 carbon atoms, and one having 6 to 12 carbon atoms is preferred and one having 6 to 10 carbon atoms is more preferred.

Specific examples of the aromatic hydrocarbon group include one or more selected from a phenyl group, a methyl phenyl group, a dimethyl phenyl group, an ethyl phenyl group, a benzyl group, a 1-phenylethyl group, a 2-phenylethyl group, a 2-phenylpropyl group, a 1-phenylbutyl group, a 4-phenylbutyl group, a 2-phenylheptyl group, a tolyl group, a xylyl group, a naphthyl group and the like.

In the ester compound (A) represented by the general formula (1), $R^1$ and $R^6$ are each a hydrocarbon group having 1 to 24 carbon atoms and may be the same or different from each other, at least one of which is preferably a linear alkyl group having 1 to 10 carbon atoms or a branched alkyl group having 3 to 8 carbon atoms, more preferably a linear alkyl group having 1 to 4 carbon atoms or a branched alkyl group having 3 to 4 carbon atoms.

In the ester compound (A) represented by the general formula (1), $R^2$ to $R^5$ are each a hydrogen atom or a hydrocarbon group having 1 to 24 carbon atoms and may be the same or different from each other, at least one of which is preferably a hydrogen atom, a linear alkyl group having 1 to 6 carbon atoms or a branched alkyl group having 3 to 6 carbon atoms, a vinyl group, a linear alkenyl group having 3 to 6 carbon atoms, a branched alkenyl group having 3 to 6 carbon atoms, a cycloalkyl group having 5 to 6 carbon atoms, a cycloalkenyl group having 5 to 6 carbon atoms, or an aromatic hydrocarbon group having 6 to 10 carbon atoms.

Also, in the ester compound (A) represented by the general formula (1), preferably at least one of $R^3$ to $R^5$ is a hydrogen atom, more preferably all of $R^3$ to $R^5$ is a hydrogen atom.

Specific examples of the ester compound (A) represented by the general formula (1) include one or more selected from ethyl 3-ethoxy-2-phenylpropionate, ethyl 3-ethoxy-2-tolylpropionate, ethyl 3-ethoxy-2-mesitylpropionate, ethyl 3-butoxy-2-(methoxyphenyl)propionate, methyl 3-isopropoxy-3-phenylpropionate, ethyl 3-ethoxy-3-phenylpropionate, ethyl 3-ethoxy-3-tert-butylpropionate, ethyl 3-ethoxy-3-adamantylpropionate, ethyl 3-ethoxy-2-isopropylpropionate, ethyl 3-ethoxy-2-tert-butylpropionate, ethyl 3-ethoxy-2-tert-aminopropionate, ethyl 3-ethoxy-2-adamantylpropionate, ethyl 3-ethoxy-2-bicyclo[2,2,1]heptylpropionate, ethyl 3-ethoxy-cyclohexane carboxylate, methyl 2-(ethoxymethyl)-cyclohexane carboxylate, and methyl 3-ethoxy-norbornane-2-carboxylate.

The solid catalyst component for olefin polymerization according to the present invention comprises a diester compound (B) represented by the following general formula (2):

$$R^7R^8C\!=\!C(COOR^9)(COOR^{10}) \qquad (2)$$

wherein $R^7$ and $R^8$ are each a hydrogen atom or a hydrocarbon group having 1 to 24 carbon atoms and may be the same or different from each other, and $R^9$ and $R^{10}$ are each a hydrocarbon group having 1 to 24 carbon atoms and may be the same or different from each other.

In the diester compound (B) represented by the general formula (2), at least one of the hydrocarbon groups having 1 to 24 carbon atoms constituting the $R^7$ to $R^{10}$ is preferably a group selected from a linear alkyl group having 1 to 24 carbon atoms, a branched alkyl group having 3 to 24 carbon atoms, a vinyl group, a linear alkenyl group having 3 to 20 carbon atoms, a branched alkenyl group having 3 to 20 carbon atoms, a cycloalkyl group having 3 to 20 carbon atoms, a cycloalkenyl group having 3 to 20 carbon atoms, and an aromatic hydrocarbon group having 6 to 20 carbon atoms.

In the diester compound (B) represented by the general formula (2), examples of the linear alkyl group having 1 to 24 carbon atoms, the branched alkyl group having 3 to 24 carbon atoms, the vinyl group, the linear alkenyl group having 3 to 20 carbon atoms, the branched alkenyl group having 3 to 20 carbon atoms, the cycloalkyl group having 3 to 20 carbon atoms, the cycloalkenyl group having 3 to 20 carbon atoms, and the aromatic hydrocarbon group having 6 to 20 carbon atoms include the same ones as those included in the description of the ester compound (A) represented by the general formula (1) described above.

In the ester compound (B) represented by the general formula (2), $R^9$ and $R^{10}$ are each a hydrocarbon group having 1 to 24 carbon atoms and may be the same or different from each other, at least one of which is preferably a linear alkyl group having 1 to 10 carbon atoms or a branched alkyl group having 3 to 8 carbon atoms, more preferably a linear alkyl group having 1 to 4 carbon atoms or a branched alkyl group having 3 to 4 carbon atoms.

Specific examples of the diester compound (B) represented by the general formula (2) include one or more selected from dimethyl propylidene malonate, diethyl propylidene malonate, di-n-propyl propylidene malonate, diisobutyl propylidene malonate, and di-n-butyl propylidene malonate; dimethyl butylidene malonate, diethyl butylidene malonate, di-n-propyl butylidene malonate, diisobutyl butylidene malonate, and di-n-butyl butylidene malonate;

dimethyl pentylidene malonate, diethyl pentylidene malonate, di-n-propyl pentylidene malonate, diisobutyl pentylidene malonate, and di-n-butyl pentylidene malonate; dimethyl hexylidene malonate, diethyl hexylidene malonate, di-n-propyl hexylidene malonate, diisobutyl hexylidene malonate, and di-n-butyl hexylidene malonate;

dimethyl (2-methylpropylidene)malonate, diethyl (2-methylpropylidene)malonate, di-n-propyl (2-methylpropylidene)malonate, diisobutyl (2-methylpropylidene)malonate, and di-n-butyl (2-methylpropylidene)malonate, and diethyl (2,2-dimethylpropylidene)malonate;

dimethyl (2-methylbutylidene)malonate, diethyl (2-methylbutylidene)malonate, di-n-propyl (2-methylbutylidene) malonate, diisobutyl (2-methylbutylidene)malonate, and di-n-butyl (2-methylbutylidene)malonate;

dimethyl (2-ethylbutylidene)malonate, diethyl (2-ethylbutylidene)malonate, di-n-propyl (2-ethylbutylidene)malonate, diisobutyl (2-ethylbutylidene)malonate, and di-n-butyl (2-ethylbutylidene)malonate;

dimethyl (2-ethylpentylidene)malonate, diethyl (2-ethylpentylidene)malonate, di-n-propyl (2-ethylpentylidene)malonate, diisobutyl (2-ethylpentylidene)malonate, and di-n-butyl (2-ethylpentylidene)malonate;

dimethyl (2-isopropylbutylidene)malonate, diethyl (2-isopropylbutylidene)malonate, di-n-propyl (2-isopropylbutylidene)malonate, diisobutyl (2-isopropylbutylidene)malonate, and di-n-butyl (2-isopropylbutylidene)malonate;

dimethyl (3-methylbutylidene)malonate, diethyl (3-methylbutylidene)malonate, di-n-propyl (3-methylbutylidene) malonate, diisobutyl (3-methylbutylidene)malonate, and di-n-butyl (3-methylbutylidene)malonate;

dimethyl (2,3-dimethylbutylidene)malonate, diethyl (2,3-dimethylbutylidene)malonate, di-n-propyl (2,3-dimethylbutylidene)malonate, diisobutyl (2,3-dimethylbutylidene) malonate, and di-n-butyl (2,3-dimethylbutylidene)malonate;

dimethyl (2-n-propylbutylidene)malonate, diethyl (2-n-propylbutylidene)malonate, di-n-propyl (2-n-propylbutylidene)malonate, diisobutyl (2-n-propylbutylidene)malonate, and di-n-butyl (2-n-propylbutylidene)malonate;

dimethyl (2-isobutyl-3-methylbutylidene)malonate, diethyl (2-isobutyl-3-methylbutylidene)malonate, di-n-propyl (2-isobutyl-3-methylbutylidene)malonate, diisobutyl (2-isobutyl-3-methylbutylidene)malonate, and di-n-butyl(2-isobutyl-3-methylbutylidene)malonate;

dimethyl (2-n-butylpentylidene)malonate, diethyl (2-n-butylpentylidene)malonate, di-n-propyl (2-n-butylpentylidene)malonate, diisobutyl (2-n-butylpentylidene)malonate, and di-n-butyl (2-n-butylpentylidene)malonate;

dimethyl (2-n-pentylhexylidene)malonate, diethyl (2-n-pentylhexylidene)malonate, di-n-propyl (2-n-pentylhexylidene)malonate, diisobutyl (2-n-pentylhexylidene)malonate, and di-n-butyl (2-n-pentylhexylidene)malonate;

dimethyl (cyclohexylmethylene)malonate, diethyl(cyclohexyl methylene)malonate, di-n-propyl (cyclohexylmethylene)malonate, diisobutyl (cyclohexylmethylene)malonate, and di-n-butyl (cyclohexylmethylene)malonate;

dimethyl (cyclopentylmethylene)malonate, diethyl (cyclopentylmethylene)malonate, di-n-propyl (cyclopentylmethylene)malonate, diisobutyl (cyclopentylmethylene)malonate, and di-n-butyl (cyclopentylmethylene)malonate;

dimethyl (1-methylpropylidene)malonate, diethyl (1-methylpropylidene)malonate, di-n-propyl (1-methylpropylidene)malonate, diisobutyl (1-methylpropylidene)malonate, di-n-butyl (1-methylpropylidene)malonate and diethyl (1-ethylpropylidene)malonate;

dimethyl (di-t-butylmethylene)malonate, diethyl (di-t-butylmethylene)malonate, di-n-propyl (di-t-butylmethylene)malonate, diisobutyl (di-t-butylmethylene)malonate, and di-n-butyl (di-t-butylmethylene)malonate;

dimethyl (diisobutylmethylene)malonate, diethyl(diisobutyl methylene)malonate, di-n-propyl (diisobutylmethylene)malonate, diisobutyl (diisobutylmethylene)malonate, and di-n-butyl (diisobutylmethylene)malonate;

dimethyl (diisopropylmethylene)malonate, diethyl (diisopropylmethylene)malonate, di-n-propyl (diisopropylmethylene)malonate, diisobutyl (diisopropylmethylene)malonate, and di-n-butyl (diisopropylmethylene)malonate;

dimethyl (dicyclopentylmethylene)malonate, diethyl (dicyclopentylmethylene)malonate, di-n-propyl (dicyclopentylmethylene)malonate, diisobutyl (dicyclopentylmethylene)malonate, and di-n-butyl(dicyclopentyl methylene)malonate;

dimethyl (dicyclohexylmethylene)malonate, diethyl (dicyclohexylmethylene)malonate, di-n-propyl (dicyclohexylmethylene)malonate, diisobutyl (dicyclohexylmethylene)malonate, and di-n-butyl (dicyclohexylmethylene)malonate;

dimethyl benzylidene malonate, diethyl benzylidene malonate, di-n-propyl benzylidene malonate, diisobutyl benzylidene malonate, and di-n-butyl benzylidene malonate;

dimethyl (1-methylbenzylidene)malonate, diethyl (1-methylbenzylidene)malonate, di-n-propyl (1-methylbenzylidene)malonate, diisobutyl (1-methylbenzylidene)malonate, and di-n-butyl (1-methylbenzylidene)malonate;

dimethyl (1-ethylbenzylidene)malonate, diethyl (1-ethylbenzylidene)malonate, di-n-propyl (1-ethylbenzylidene)malonate, diisobutyl (1-ethylbenzylidene)malonate, and di-n-butyl (1-ethylbenzylidene)malonate;

dimethyl (1-n-propylbenzylidene)malonate, diethyl (1-n-propylbenzylidene)malonate, di-n-propyl (1-n-propylbenzylidene)malonate, diisobutyl (1-n-propylbenzylidene)malonate, and di-n-butyl (1-n-propylbenzylidene)malonate;
dimethyl (1-isopropylbenzylidene)malonate, diethyl (1-isopropylbenzylidene)malonate, di-n-propyl (1-isopropylbenzylidene)malonate, diisobutyl (1-isopropylbenzylidene)malonate, and di-n-butyl (1-isopropylbenzylidene)malonate;

dimethyl (1-n-butylbenzylidene)malonate, diethyl (1-n-butylbenzylidene)malonate, di-n-propyl (1-n-butylbenzylidene)malonate, diisobutyl (1-n-butylbenzylidene)malonate, and di-n-butyl (1-n-butylbenzylidene)malonate;

dimethyl (1-isobutylbenzylidene)malonate, diethyl (1-isobutylbenzylidene)malonate, di-n-propyl (1-isobutylbenzylidene)malonate, diisobutyl (1-isobutylbenzylidene)malonate, and di-n-butyl (1-isobutylbenzylidene)malonate;

dimethyl (1-t-butylbenzylidene)malonate, diethyl (1-t-butylbenzylidene)malonate, di-n-propyl (1-t-butylbenzylidene)malonate, diisobutyl (1-t-butylbenzylidene)malonate, and di-n-butyl (1-t-butylbenzylidene)malonate;

dimethyl (1-n-pentylbenzylidene)malonate, diethyl (1-n-pentylbenzylidene)malonate, di-n-propyl (1-n-pentylbenzylidene)malonate, diisobutyl (1-n-pentylbenzylidene)malonate, and di-n-butyl (1-n-pentylbenzylidene)malonate;

dimethyl (2-methylphenylmethylene)malonate, diethyl (2-methylphenylmethylene)malonate, di-n-propyl (2-methylphenylmethylene)malonate, diisobutyl (2-methylphenylmethylene)malonate, di-n-butyl (2-methylphenylmethylene)malonate, and dimethyl (4-methylphenylmethylene)malonate;

dimethyl (2,6-dimethylphenylmethylene)malonate, diethyl (2,6-dimethylphenylmethylene)malonate, di-n-propyl (2,6-dimethylphenylmethylene)malonate, diisobutyl (2,6-dimethylphenylmethylene)malonate, and di-n-butyl (2,6-dimethylphenylmethylene)malonate;

dimethyl (1-methyl-1-(2-methylphenyl)methylene)malonate, diethyl (1-methyl-1-(2-methylphenyl)methylene)malonate, di-n-propyl (1-methyl-1-(2-methylphenyl)methylene)malonate, diisobutyl (1-methyl-1-(2-methylphenyl)methylene)malonate, and di-n-butyl (1-methyl-1-(2-methylphenyl)methylene)malonate;

dimethyl (2-methylcyclohexylmethylene)malonate, diethyl (2-methylcyclohexylmethylene)malonate, di-n-propyl (2-methylcyclohexylmethylene)malonate, diisobutyl (2-methylcyclohexylmethylene)malonate, and di-n-butyl (2-methylcyclohexylmethylene)malonate;

dimethyl (2,6-dimethylcyclohexylmethylene)malonate, diethyl (2,6-dimethylcyclohexylmethylene)malonate, di-n-propyl (2,6-dimethylcyclohexylmethylene)malonate, diisobutyl (2,6-dimethylcyclohexylmethylene)malonate, and di-n-butyl (2,6-dimethylcyclohexylmethylene)malonate;

dimethyl (1-methyl-1-(2-methylcyclohexyl)methylene)malonate, diethyl (1-methyl-1-(2-methylcyclohexyl)methylene)malonate, di-n-propyl (1-methyl-1-(2-methylcyclohexyl)methylene)malonate, diisobutyl (1-methyl-1-(2-methylcyclohexyl)methylene)malonate, and di-n-butyl (1-methyl-1-(2-methylcyclohexyl)methylene)malonate;

dimethyl (naphthylmethylene)malonate, diethyl (naphthylmethylene)malonate, di-n-propyl(naphthyl methylene)malonate, diisobutyl (naphthylmethylene)malonate, and di-n-butyl (naphthylmethylene)malonate; and dimethyl (1-n-hexylbenzylidene)malonate, diethyl (1-n-hexylbenzylidene)malonate, di-n-propyl (1-n-hexylbenzylidene)malonate, diisobutyl (1-n-hexylbenzylidene)malonate, and di-n-butyl (1-n-hexylbenzylidene)malonate.

The solid catalyst component for olefin polymerization (I) according to the present invention comprises an ester compound (A) represented by the general formula (1) and a diester compound (B) represented by the general formula (2) as electron-donating compounds and may comprise an electron-donating compound other than those (hereinafter appropriately referred to as "electron-donating compound (D)").

Examples of the electron-donating compound (D) include acid halides, acid amines, nitriles, acid anhydrides, diether compounds and carboxylates other than the diester compound (B) represented by the general formula (2).

Specific examples of the electron-donating compound (D) include one or more selected from a dicarboxylic acid diester such as a succinic acid diester, a cycloalkane dicarboxylic acid diester, a cycloalkene dicarboxylic acid diester, a malonic acid diester, an alkyl-substituted malonic acid diester and a maleic acid diester, a diether compound and the like.

As the electron-donating compound (D), one or more selected from a succinic acid diester such as diethyl diisopropyl succinate, a dialkyl malonic acid diester such as dimethyl diisobutyl malonate and diethyl diisobutyl malonate, a maleic acid diester such as diethyl maleate, a cycloalkane dicarboxylic acid diester such as dimethyl cyclohexane-1,2-dicarboxylate, and a 1,3-diether such as (isopropyl)(isopentyl)-1,3-dimethoxypropane and 9,9-bis(methoxymethyl)fluorene are preferred.

Since the solid catalyst component for olefin polymerization according to the present invention comprises the electron-donating compound (D) together with an ester compound (A) represented by the general formula (1) and a diester compound (B) represented by the general formula (2), the stereoregularity of an olefin polymer to be obtained in polymerization can be easily improved and the molecular weight distribution and the hydrogen responsiveness can be easily controlled in the ranges similar to those of a polymer produced using a solid catalyst including a conventional phthalate as the electron donor.

As described above, although the solid catalyst component for olefin polymerization according to the present invention may comprise a plurality of electron-donating compounds, the proportion of the total content of the ester compound (A) represented by the general formula (1) and the diester compound (B) represented by the general formula (2) in the whole content of the electron-donating compounds represented by the following expression is preferably 50 to 100 mass %, more preferably 80 to 100 mass %, furthermore preferably 90 to 100 mass %:

{(content (g) of ester compound (A)+content (g) of ester compound (B))/(whole content (g) of electron-donating compounds)}×100.

The solid catalyst component for olefin polymerization according to the present invention has a proportion of the total content of the ester compound (A) represented by the general formula (1) and the diester compound (B) represented by the general formula (2) in the whole content of the electron-donating compounds in the range described above, so that a solid catalyst component for olefin polymerization excellent in the olefin-polymerizing activity, with the primary physical properties of the resulting polymer such as stereoregularity and molecular weight distribution controlled in desired ranges, can be easily provided.

The solid catalyst component for olefin polymerization according to the present invention comprises an ester compound (A) represented by the general formula (1) and a diester compound (B) represented by the general formula (2) so that a ratio represented by the following expression:

(content (mass %) of ester compound (A)/content (mass %) of diester compound (B))

is 0.05 to 50, preferably 0.1 to 25, more preferably 0.5 to 20.

The solid catalyst component for olefin polymerization according to the present invention comprises an ester compound (A) represented by the general formula (1) and a diester compound (B) represented by the general formula (2) at the ratio described above, so that a solid catalyst component for olefin polymerization excellent in the olefin-polymerizing activity, with the primary physical properties of the resulting polymer such as stereoregularity and molecular weight distribution controlled in desired ranges, can be provided.

The solid catalyst component for olefin polymerization according to the present invention may comprise a polysiloxane (hereinafter appropriately referred to as "polysiloxane (E)").

When an olefin is polymerized, the solid catalyst component for olefin polymerization according to the present invention can easily improve the stereoregularity or the crystallinity of a produced polymer to be obtained, and easily reduces a fine powder of the produced polymer, due to containing a polysiloxane (E).

The polysiloxane is a polymer having a siloxane bond (—Si—O— bond) in a main chain and also referred to as a silicone oil, having a viscosity at 25° C. of 0.02 to 100 cm$^2$/s (2 to 10000 centistokes), more preferably 0.03 to 5 cm$^2$/s (3 to 500 centistokes), which is a chain, partially hydrogenated, cyclic or modified polysiloxane in a liquid or viscous state at normal temperature.

Examples of the chain polysiloxane include dimethyl polysiloxane and methyl phenyl polysiloxane, examples of the partially hydrogenated polysiloxane include methyl hydrogen polysiloxane having a hydrogenation rate of 10 to 80%, and examples of the cyclic polysiloxane include hexamethyl cyclotrisiloxane, octamethyl cyclotetrasiloxane, decamethyl cyclopentasiloxane, 2,4,6-trimethyl cyclotrisiloxane, and 2,4,6,8-tetramethyl cyclotetrasiloxane.

Preferably, the solid catalyst component for olefin polymerization according to the present invention is a material comprising a magnesium compound (C), a titanium halogen compound (F), an ester compound (A) represented by the general formula (1), and a diester compound (B) represented by the general formula (2), i.e., a contact product thereof.

Examples of the magnesium compound (C) include one or more selected from a dihalogenated magnesium, a dialkyl magnesium, a halogenated alkyl magnesium, a dialkoxy magnesium, diaryloxy magnesium, a halogenated alkoxy magnesium, a magnesium salt of fatty acid and the like.

Among these magnesium compounds, a dihalogenated magnesium, a mixture of a dihalogenated magnesium and a dialkoxy magnesium, and a dialkoxy magnesium are preferred, and particularly a dialkoxy magnesium is preferred. Specific examples thereof include dimethoxy magnesium, diethoxy magnesium, dipropoxy magnesium, dibutoxy magnesium, ethoxy methoxy magnesium, ethoxy propoxy magnesium, butoxy ethoxy magnesium and the like, and among them, diethoxy magnesium is particularly preferred.

The dialkoxy magnesium may be obtained by causing a reaction of metal magnesium with an alcohol in the presence of a halogen-containing organic metal or the like.

Furthermore, the dialkoxy magnesium is in a granular or powder form with an amorphous or spherical shape. For example, with use of a dialkoxy magnesium in a spherical shape, a polymerized powder having a better particle shape and a narrow particle size distribution can be more easily obtained, so that with improved the handleability of the produced polymerized powder in polymerization operation, a problem such as filter clogging in an apparatus for separating a polymer resulting from a fine powder included in the produced polymerized powder can be easily solved.

The dialkyoxy magnesium may be used singly or in combination of two or more.

The spherical dialkoxy magnesium is not necessarily in a truly spherical shape, and may be in an ellipsoidal shape or a potato shape. Specifically, the particle shape has a ratio of the major axis diameter L to the minor axis diameter W, i.e., (L/W), of preferably 3 or less, more preferably 1 to 2, furthermore preferably 1 to 1.5.

Furthermore, the dialkoxy magnesium has an average particle diameter D50 (particle diameter at a cumulative particle size of 50% in volume cumulative particle size distribution) of preferably 1 to 200 μm, more preferably 5 to 150 μm, when measured using a laser light scattering diffraction particle size analyzer.

If the dialkoxy magnesium is in a spherical shape, the average particle diameter thereof is preferably 1 to 100 μm, more preferably 5 to 50 μm, furthermore preferably 10 to 40 μm.

Also, regarding the particle size of the dialkyoxy magnesium, a narrow particle size distribution with a less amount of a fine powder and a coarse powder is preferred.

Specifically, when measured using a laser light scattering diffraction particle size analyzer, the content of particles of 5 μm or less is preferably 20% or less, more preferably 10% or less. Meanwhile, the content of particles of 100 μm or more is preferably 10% or less, more preferably 5% or less.

Furthermore, the particle size distribution represented by D90/D10 (herein, D90 represents the particle diameter at a cumulative particle size of 90%, and D10 represents the particle size at a cumulative particle size of 10%) is preferably 3 or less, more preferably 2 or less.

A method for producing the spherical dialkoxy magnesium described above is exemplified, for example, in Japanese Patent Laid-Open No. 58-4132, Japanese Patent Laid-Open No. 62-51633, Japanese Patent Laid-Open No. 3-74341, Japanese Patent Laid-Open No. 4-368391, and Japanese Patent Laid-Open No. 8-73388.

In the solid catalyst component for olefin polymerization according to the present invention, the magnesium compound (C) may be any of a magnesium compound in a solution state and a suspension of a magnesium compound. If the magnesium compound (C) is in a solid state, the magnesium compound (C) is dissolved in a solvent having the capability to solubilize the magnesium compound (C) to make a magnesium compound in a solution state, or suspended in a solvent having no capability to solubilize the magnesium compound (C) to make a suspension of the magnesium compound for use. If the magnesium compound (C) is a liquid, the magnesium compound (C) may be directly used as a magnesium compound in a solution state, or may be dissolved in a solvent capable of solubilizing the magnesium compound for use as a magnesium compound in a solution state.

Examples of a compound capable of solubilizing the magnesium compound (C) in a solid state include at least one compound selected from the group consisting of an alcohol, an ether and an ester. Specifically, an alcohol having 1 to 18 carbon atoms such as methanol, ethanol, propanol, butanol, pentanol, hexanol, 2-ethylhexanol, octanol, dodecanol, octadecyl alcohol, oleyl alcohol, benzyl alcohol, phenylethyl alcohol, cumyl alcohol, isopropyl alcohol, isopropylbenzyl alcohol, and ethylene glycol; a halogen-containing alcohol having 1 to 18 carbon atoms such as trichloromethanol, trichloroethanol and trichlorohexanol; an ether having 2 to 20 carbon atoms such as methyl ether, ethyl ether, isopropyl ether, butyl ether, amyl ether, tetrahydrofuran, ethyl benzyl ether, dibutyl ether, anisole and diphenyl ether; a metal acid ester such as tetraethoxy titanium, tetra-n-propoxy titanium, tetraisopropoxy titanium, tetrabutoxy titanium, tetrahexoxy titanium, tetrabutoxy zirconium and tetraethoxy zirconium; and among them, an alcohol such as ethanol, propanol, butanol and 2-ethylhexanol is preferred, and 2-ethylhexanol is particularly preferred.

Meanwhile, as the medium incapable of solubilizing the magnesium compound (C), a saturated hydrocarbon solvent or an unsaturated hydrocarbon solvent that dissolves no magnesium compound is used.

A saturated hydrocarbon solvent or an unsaturated hydrocarbon solvent has high safety and high industrial versatility, and specific examples thereof include a linear or branched aliphatic hydrocarbon compound having a boiling point of 50 to 200° C. such as hexane, heptane, decane and methylheptane, an alicyclic hydrocarbon compound having a boiling point of 50 to 200° C. such as cyclohexane, ethyl cyclohexane and decahydronaphthalene, and an aromatic hydrocarbon compound having a boiling point of 50 to 200° C. such as toluene, xylene and ethylbenzene. In particular, examples include one or more selected from a linear aliphatic hydrocarbon compound having a boiling point of 50 to 200° C. such as hexane, heptane and decane, and an aromatic hydrocarbon compound having a boiling point of 50 to 200° C. such as toluene, xylene and ethylbenzene.

The titanium halogen compound (F) is not particularly limited, and examples thereof include one or more selected from a titanium tetrahalide, an alkoxy titanium halide and the like.

Preferably, the titanium halogen compound (F) is one compound selected from the group consisting of a titanium tetrahalide or an alkoxy titanium halide represented by a general formula $Ti(OR^{25})_iX_{4-i}$, wherein $R^{25}$ represents a hydrocarbon group having 1 to 10 carbon atoms, X represents a halogen atom, and if a plurality of X are present, each X may be the same or different, and i is an integer of 0 to 4.

Specific examples of the titanium halogen compound (F) include one or more selected from a titanium tetrahalide such as titanium tetrafluoride, titanium tetrachloride, titanium tetrabromide and titanium tetraiodide; as an alkoxy titanium halide, an alkoxy titanium trihalide such as methoxy titanium trichloride, ethoxy titanium trichloride, propoxy titanium trichloride and n-butoxy titanium trichloride; a dialkoxy titanium dihalide such as dimethoxy titanium dichloride, diethoxy titanium dichloride, dipropoxy titanium dichloride and di-n-butoxy titanium dichloride; a trialkoxy titanium halide such as trimethoxy titanium chloride, triethoxy titanium chloride, tripropoxy titanium chloride and tri-n-butoxy titanium chloride; and the like.

Among them, a halogen-containing titanium compound is preferably used. A titanium tetrahalide such as titanium tetrachloride, titanium tetrabromide and titanium tetraiodide is preferred, and titanium tetrachloride is more preferred. These titanium compounds may be diluted with a hydrocarbon compound, a halogenated hydrocarbon compound or the like for use.

The solid catalyst component for olefin polymerization according to the present invention may include a halogen compound other than the titanium halogen compound (F) contacted on an as-needed basis. Examples of the halogen compound include a tetravalent halogen-containing silicon compound, and more specifically, one or more selected from a silane tetrahalide such as tetrachlorosilane (silicon tetrachloride) and tetrabromosilane; an alkoxy group-containing halogenated silane such as methoxy trichlorosilane, ethoxy trichlorosilane, propoxy trichlorosilane, n-butoxy trichlorosilane, dimethoxy dichlorosilane, diethoxy dichlorosilane, dipropoxy dichlorosilane, di-n-butoxy dichlorosilane, trimethoxy chlorosilane, triethoxy chlorosilane, tripropoxy chlorosilane, and tri-n-butoxy chlorosilane; and the like.

Preferably, the solid catalyst component for olefin polymerization according to the present invention is prepared by contacting the magnesium compound (C), the titanium halogen compound (F) described above, and the ester compound (A) represented by the general formula (1), the diester compound (B) represented by the general formula (2), and, on an as-needed basis, a polysiloxane (E) in the presence of an inert organic solvent.

As the inert organic solvent, one in which the titanium halogen compound (F) is dissolved and the magnesium compound (C) is not dissolved is preferred. Specific examples thereof include one or more selected from a saturated hydrocarbon compound such as pentane, hexane, heptane, octane, nonane, decane, cyclohexane, methylcyclohexane, ethylcyclohexane, 1,2-diethylcyclohexane, methylcyclohexene, decalin and a mineral oil, an aromatic hydrocarbon compound such as benzene, toluene, xylene and ethylbenzene, a halogenated hydrocarbon compound such as orthodichlorobenzene, methylene chloride, 1,2-dichlorobenzene, carbon tetrachloride and dichloroethane, and the like.

As the inert organic solvent, a saturated hydrocarbon compound or an aromatic hydrocarbon compound in a liquid state at normal temperature, having a boiling point of about 50 to 200° C., is preferably used. Among them, one or more selected from hexane, heptane, octane, ethyl cyclohexane, a mineral oil, toluene, xylene and ethyl benzene are preferred.

Examples of a method for preparing the solid catalyst component for olefin polymerization according to the present invention include: a method for cogrinding a solid magnesium compound having no reducing properties, an ester compound (A), a diester compound (B) and a halogenated titanium; a method for contacting a halogenated magnesium compound having an adduct such as alcohol, an ester compound (A), a diester compound (B) and a halogenated titanium in the co-presence of an inert hydrocarbon solvent; a method for contacting a dialkoxy magnesium, an ester compound (A), a diester compound (B) and a halogenated titanium in the co-presence of an inert hydrocarbon solvent; and a method for contacting a magnesium compound having reducing properties, an ester compound (A), a diester compound (B) and a halogenated titanium to precipitate a solid catalyst.

Specific methods for preparing the solid catalyst component for olefin polymerization according to the present invention (1) to (16) are exemplified as follows.

In the following methods (1) to (16), in addition to an ester compound (A) and a diester compound (B), an electron-donating compound other than them may be used together. The contact may be performed in the co-presence of, for example, another reaction reagent of silicon, phosphorus and aluminum, or a surfactant.

(1) A method for preparing the solid catalyst component for olefin polymerization according to the present invention including dissolving a halogenated magnesium in an alkoxy titanium compound and then contacting an organosilicon compound with the solution to obtain a solid product, causing a reaction of the solid product with a halogenated titanium, and subsequently causing a contact reaction with an ester compound (A) and a diester compound (B).

On this occasion, an organoaluminum compound, an organosilicon compound and an olefin may be further added to the solid catalyst component for olefin polymerization to perform a preliminary polymerization treatment.

(2) A method for preparing the solid catalyst component for olefin polymerization according to the present invention including causing a reaction of a halogenated magnesium with an alcohol to make a uniform solution and then contacting a carboxylic anhydride with the uniform solution, subsequently causing a contact reaction of the solution with a halogenated titanium, an ester compound (A) and a diester compound (B) to obtain a solid, and bringing the solid into further contact with a halogenated titanium.

(3) A method for preparing the solid catalyst component for olefin polymerization according to the present invention including causing a reaction of metallic magnesium, butyl chloride and an dialkyl ether to synthesize an organomagnesium compound, causing a contact reaction of the organomagnesium compound with alkoxy titanium to obtain a solid product, and causing a contact reaction of the solid product with an ester compound (A), a diester compound (B), and a halogenated titanium.

On this occasion, the solid component may be subjected to a preliminary polymerization treatment with an organoaluminum compound, an organosilicon compound and an olefin to prepare the solid catalyst component for olefin polymerization according to the present invention.

(4) A method for obtaining the solid catalyst component for olefin polymerization according to the present invention including causing a contact reaction of an organomagnesium compound such as a dialkyl magnesium and an organoaluminum compound with an alcohol in the presence of a hydrocarbon solvent to make a uniform solution, contacting the solution with a silicon compound such as silicon tetrachloride to obtain a solid product, subsequently causing a contact reaction of the solid product with a halogenated titanium, an ester compound (A) and a diester compound (B) in the presence of an aromatic hydrocarbon solvent, and then bringing the solid product into further contact with titanium tetrachloride.

(5) A method for obtaining the solid catalyst component for olefin polymerization according to the present invention including causing a contact reaction of magnesium chloride, a tetraalkoxy titanium and an aliphatic alcohol in the presence of a hydrocarbon solvent to make a uniform solution, contacting the solution with a halogenated titanium, then raising the temperature of the solution to deposit a solid, contacting the solid with an ester compound (A) and a diester compound (B), and causing a further reaction with a halogenated titanium.

(6) A method for preparing the solid catalyst component for olefin polymerization according to the present invention including causing a contact reaction of a metallic magnesium powder, an alkyl monohalogen compound and iodine, then causing a contact reaction of a tetraalkoxy titanium, an acid halide and an aliphatic alcohol in the presence of a hydrocarbon solvent to make a uniform solution, adding titanium tetrachloride to the solution, then raising the temperature of the solution to deposit a solid product, contacting the solid product with an ester compound (A) and a diester compound (B), and causing a further reaction with titanium tetrachloride.

(7) A method for preparing the solid catalyst component for olefin polymerization according to the present invention including suspending a dialkoxy magnesium in a hydrocarbon solvent, then contacting the suspension with titanium tetrachloride followed by raising the temperature, then contacting the suspension with an ester compound (A) and a diester compound (B) to obtain a solid product, washing the solid product with a hydrocarbon solvent, then contacting the solid product with titanium tetrachloride again.

On this occasion, the solid component may be heat treated in the presence or absence of a hydrocarbon solvent.

(8) A method for obtaining the solid catalyst component for olefin polymerization according to the present invention including suspending a dialkoxy magnesium in a hydrocarbon solvent, then causing a contact reaction of the suspension with a halogenated titanium, an ester compound (A) and a diester compound (B) to obtain a solid product, washing the solid product with an inert organic solvent, and then contacting the solid product with a halogenated titanium again to cause a reaction in the presence of a hydrocarbon solvent.

On this occasion, the solid component may be contacted with a halogenated titanium two or more times.

(9) A method for preparing the solid catalyst component for olefin polymerization according to the present invention including cogrinding a dialkoxy magnesium, calcium chloride and an alkoxy group-containing silicon compound, suspending a ground solid thus obtained in a hydrocarbon solvent, then causing a contact reaction of the suspension with a halogenated titanium, an ester compound (A) and a diester compound (B), and subsequently bringing the product into further contact with a halogenated titanium.

(10) A method for obtaining the solid catalyst component for olefin polymerization according to the present invention including suspending dialkoxy magnesium, an ester compound (A) and a diester compound (B) in a hydrocarbon solvent, contacting the suspension with a halogenated titanium to cause a reaction to obtain a solid, washing the solid product with a hydrocarbon solvent, and then bringing the solid into further contact with a halogenated titanium in the presence of a hydrocarbon solvent.

(11) A method for preparing the solid catalyst component for olefin polymerization according to the present invention including causing a contact reaction of an aliphatic magnesium such as magnesium stearate with a halogenated titanium, an ester compound (A) and a diester compound (B), and then bringing the product into further contact with a halogenated titanium.

(12) A method for preparing the solid catalyst component for olefin polymerization according to the present invention including suspending a dialkoxy magnesium in a hydrocarbon solvent, contacting the suspension with a halogenated titanium followed by raising the temperature, then causing a contact reaction of the suspension with an ester compound (A) and a diester compound (B) to obtain a solid product, washing the solid product with a hydrocarbon solvent, then contacting the product with a halogenated titanium again to prepare a solid catalyst component for olefin polymerization (I), wherein aluminum chloride is contacted in any of the steps of the suspension, contacting and contact reaction.

(13) A method for preparing the solid catalyst component for olefin polymerization according to the present invention including causing a contact reaction of a dialkoxy magnesium, 2-ethylhexyl alcohol, and carbon dioxide in the presence of a hydrocarbon solvent to make a uniform solution, causing a contact reaction of the solution with a halogenated titanium, an ester compound (A) and a diester compound (B) to obtain a solid, dissolving the solid in tetrahydrofuran, then further depositing a solid product, causing a contact reaction of the solid product with a halogenated titanium, and repeating the contact reaction with the halogenated titanium on an as-needed basis.

On this occasion, in any of the steps of the contacting, contact reaction, and dissolution, a silicon compound such as tetrabutoxysilane may be used.

(14) A method for obtaining the solid catalyst component for olefin polymerization according to the present invention including suspending magnesium chloride, an organic epoxy compound and a phosphate compound in a hydrocarbon solvent, then heating the suspension to make a uniform solution, causing a contact reaction of the solution with a carboxylic anhydride and a halogenated titanium to obtain a solid product, contacting the solid product with an ester compound (A) and a diester compound (B) to cause a reaction, washing a reaction product thus obtained with a hydrocarbon solvent, and then contacting the product with the halogenated titanium again in the presence of a hydrocarbon solvent.

(15) A method for obtaining the solid catalyst component for olefin polymerization according to the present invention including causing a contact reaction of dialkoxy magnesium, a titanium compound, an ester compound (A) and a diester compound (B) in the presence of a hydrocarbon solvent, causing a contact reaction of the reaction product thus obtained with a silicon compound such as a polysiloxane (E), causing a further contact reaction of the product with a halogenated titanium, subsequently causing a contact reaction of the product with a metallic salt of an organic acid, and then contacting the product with the halogenated titanium again.

(16) A method for preparing the solid catalyst component for olefin polymerization according to the present invention including suspending a dialkoxy magnesium, an ester compound (A) and a diester compound (B) in a hydrocarbon solvent followed by raising the temperature, then contacting the suspension with a halogenated silicon and subsequently with a halogenated titanium to obtain a solid product, washing the solid product with a hydrocarbon solvent, then contacting the product with the halogenated titanium again in the presence of a hydrocarbon solvent.

On this occasion, the solid component may be heat treated in the presence or absence of a hydrocarbon solvent.

In order to further improve the polymerizing activity in olefin polymerization and the stereoregularity of a produced polymer, in the methods (1) to (16) described above, the solid catalyst component for olefin polymerization after washing may be contacted with a halogenated titanium and a hydrocarbon solvent over again at 20 to 100° C., and after a reaction treatment (secondary reaction treatment) at a raised temperature, the solid catalyst component may be subjected to a washing operation with an inert organic solvent in a liquid state at normal temperature, with a repetition of 1 to 10 times.

As the method for preparing the solid catalyst component for olefin polymerization according to the present invention, any of the methods described above can be suitably used. Among them, the methods (1), (3), (4), (5), (7), (8) and (10) are preferred, and the methods (3), (4), (7), (8) and (10) are particularly preferred from the viewpoint of obtaining a solid catalyst component for olefin polymerization having a high stereoregularity.

Among these preparation methods, examples of the method for obtaining the solid catalyst component for olefin polymerization according to the present invention include suspending a dialkoxy magnesium, an ester compound (A) and a diester compound (B) in a hydrocarbon solvent selected from a linear hydrocarbon, a branched aliphatic hydrocarbon, an alicyclic hydrocarbon, and an aromatic hydrocarbon, adding the suspension into a halogenated titanium to cause a reaction to obtain a solid, and after washing the solid product with a hydrocarbon solvent, bringing the product into further contact with a halogenated titanium in the presence of a hydrocarbon solvent.

The resulting product is formed into a powdery solid component by removing the remaining solvent so that the mass ratio is 1/3 or less, preferably 1/20 to 1/6 to the solid component. It is preferable to remove fine powder having a particle diameter of 11 μm or less and mixed to the powdery solid component by a method such as air classification.

Although the ratio of the amount to be used of the components varies depending on the above methods of preparing a solid catalyst component for olefin polymerization and thus cannot be definitely determined, the amount of titanium halide compound (F), for example, is preferably 0.5 to 100 mol, more preferably 0.5 to 50 mol, and further preferably 1 to 10 mol per mol of magnesium compound (C). The total amount of ester compound (A), diester compound (B) and other electron-donating compounds (D) is preferably 0.01 to 10 mol, more preferably 0.01 to 1 mol, and further preferably 0.02 to 0.6 mol per mol of magnesium compound (C). Furthermore, the amount of solvent, for example, is preferably 0.001 to 500 mol, more preferably 0.001 to 100 mol, further preferably 0.005 to 10 mol per mol of magnesium compound (C). The amount of polysiloxane (E) is preferably 0.01 to 100 g, more preferably 0.05 to 80 g, and further preferably 1 to 50 g per mol of magnesium compound (C).

The content of a titanium atom, a magnesium atom, a halogen atom, ester compound (A) represented by the general formula (1), and a diester compound represented by the general formula (2) in the solid catalyst component for olefin polymerization according to the present invention is not particularly limited.

The solid catalyst component for olefin polymerization according to the present invention contains preferably 0.1 to 10 mass %, more preferably 0.5 to 8.0 mass %, and further preferably 1.0 to 8.0 mass % of a titanium atom.

The solid catalyst component for olefin polymerization according to the present invention contains preferably 10 to 70 mass %, more preferably 10 to 50 mass %, further preferably 15 to 40 mass %, and even more preferably 15 to 25 mass % of a magnesium atom.

The solid catalyst component for olefin polymerization according to the present invention contains preferably 20 to 90 mass %, more preferably 30 to 85 mass %, further preferably 40 to 80 mass %, and even more preferably 45 to 75 mass % of a halogen atom.

The solid catalyst component for olefin polymerization according to the present invention contains preferably 0.1 to 25 mass %, more preferably 1 to 20 mass %, and further preferably 2 to 15 mass % of ester compound (A) represented by the general formula (1).

The solid catalyst component for olefin polymerization according to the present invention contains preferably 0.1 to 25 mass %, more preferably 1 to 20 mass %, and further preferably 2 to 15 mass % of diester compound (B) represented by the general formula (2).

As used herein, the content of a titanium atom and the content of a magnesium atom in the solid catalyst component for olefin polymerization means values measured according to JIS 8311-1997 "Method for determination of titanium in titanium ores" (redox titration).

Furthermore, as used herein, the content of a halogen atom in the solid catalyst component for olefin polymerization means values measured by titration with silver nitrate in which the solid catalyst component is treated with a mixed solution of sulfuric acid and pure water to prepare an aqueous solution thereof and a halogen atom in an aliquot of the solution is titrated with a standard solution of silver nitrate.

As used herein, the content of the electron-donating compound such as ester compound (A) and diester compound (B) in the solid catalyst component for olefin polymerization means a value obtained by hydrolyzing the solid catalyst, then extracting an internal electron donor with an aromatic solvent, and subjecting the solution to measurement by gas chromatography FID (Flame Ionization Detector).

The present invention provides a solid catalyst component for olefin polymerization comprising an electron-donating compound other than a phthalate, the solid catalyst component being equal in the olefin-polymerizing activity and in the primary physical properties of the resulting polymer such as stereoregularity and molecular weight distribution to those with use of a phthalate as an electron-donating compound.

Next, the catalyst for olefin polymerization according to the present invention will be described.

The catalyst for olefin polymerization according to the present invention comprises:
(I) the solid catalyst component for olefin polymerization according to the present invention;
(II) an organoaluminum compound represented by the following general formula (3):

  (3)

wherein $R^{11}$ is an alkyl group having 1 to 6 carbon atoms; Q is a hydrogen atom or a halogen atom; p is a real number satisfying $0<p\leq 3$; if a plurality of $R^{11}$ are present, $R^{11}$ may be the same or different from each other; and if a plurality of Q are present, Q may be the same or different from each other; and
(III) an external electron-donating compound.

The details of (I) the solid catalyst component for olefin polymerization according to the present invention constituting the catalyst for olefin polymerization according to the present invention are as described above.

In the catalyst for olefin polymerization according to the present invention, (II) the organoaluminum compound is represented by the following general formula (3):

  (3)

wherein $R^{11}$ is an alkyl group having 1 to 6 carbon atoms; Q is a hydrogen atom or a halogen atom; p is a real number satisfying $0<p\leq 3$; if a plurality of $R^{11}$ are present, $R^{11}$ may be the same or different from each other; and if a plurality of Q are present, Q may be the same or different from each other.

Examples of (II) organoaluminum compounds include at least one selected from trialkylaluminum such as triethylaluminum, triisopropylaluminum, tri-n-butylaluminum, tri-n-hexylaluminum and triisobutylaluminum, alkylaluminum halide such as diethylaluminum chloride and diethylaluminum bromide, and diethylaluminum hydride. At least one selected from alkylaluminum halide such as diethylaluminum chloride and trialkylaluminum such as triethylaluminum, tri-n-butylaluminum and triisobutylaluminum is preferred, and at least one selected from triethylaluminum and triisobutylaluminum is more preferred.

Examples of (III) external electron-donating compounds constituting the catalyst for olefin polymerization according to the present invention include at least one selected from organic compounds containing an oxygen atom or a nitrogen atom.

Ester compound (A) represented by the general formula (1) and diester compound (B) represented by the general formula (2) may be used as the external electron-donating compound described above. Other examples thereof include at least one selected from alcohol, phenol, ether, ester, ketone, acid halide, aldehyde, amine, amide, nitrile, isocyanate, and an organosilicon compound having a Si—O—C bond or Si—N—C bond. At least one selected from esters such as ethyl benzoate, ethyl p-methoxybenzoate, ethyl p-ethoxybenzoate, methyl p-toluylate, ethyl p-toluylate, methyl anisate and ethyl anisate, 1,3-diether compounds and organosilicon compounds is more preferred. At least one selected from 1,3-diether compounds, alkoxysilane compounds having a Si—O—C bond and aminosilane compounds having a Si—N—C bond is more preferred.

Examples of (III) external electron-donating compounds described above include at least one selected from organosilicon compounds (alkoxysilane compounds having a Si—O—C bond) represented by the following general formula (4):

  (4)

wherein $R^{12}$ is any of a linear alkyl group having 1 to 12 carbon atoms, a branched alkyl group having 3 to 12 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and q is an integer satisfying $0\leq q\leq 3$, and if q is 2 or more, a plurality of $R^{12}$ may be the same or different from each other; and $R^{13}$ represents any of a linear alkyl group having 1 to 4 carbon atoms, a branched alkyl group having 3 to 4 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and a plurality of $R^{13}$ may be the same or different from each other.

Examples of (III) external electron-donating compound described above also include at least one selected from organosilicon compounds (aminosilane compounds having a Si—N—C bond) represented by the following general formula (5):

$(R^{14}R^{15}N)_sSiR^{16}_{4-s}$ (5)

wherein $R^{14}$ and $R^{15}$ are each any of a hydrogen atom, a linear alkyl group having 1 to 12 carbon atoms, a branched alkyl group having 3 to 12 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and $R^{14}$ and $R^{15}$ may be the same or different from each other and may be bonded to each other to form a ring; and $R^{16}$ is any of a linear alkyl group having 1 to 12 carbon atoms or a branched alkyl group having 3 to 12 carbon atoms, a vinyl group, an alkenyl group having 3 to 12 carbon atoms, a cycloalkyl group having 3 to 12 carbon atoms, an aromatic hydrocarbon group having 6 to 12 carbon atoms, a linear alkoxy group having 1 to 12 carbon atoms or a branched alkoxy group having 3 to 12 carbon atoms, a vinyloxy group, an allyloxy group having 3 to 12 carbon atoms, and an aryloxy group having 6 to 12 carbon atoms, and if a plurality of $R^{16}$ are present, $R^{16}$ may be the same or different from each other, and s is an integer of 1 to 3.

Examples of such organosilicon compounds include phenylalkoxysilane, alkylalkoxysilane, phenylalkylalkoxysilane, cycloalkylalkoxysilane, alkyl(cycloalkyl)alkoxysilane, (alkylamino)alkoxysilane, alkyl(alkylamino)alkoxysilane, cycloalkyl(alkylamino)alkoxysilane, tetraalkoxysilane, tetrakis(alkylamino)silane, alkyltris(alkylamino)silane, dialkylbis(alkylamino)silane, and trialkyl(alkylamino)silane. These are more specifically phenyltrimethoxysilane, t-butyltrimethoxysilane, diisopropyldimethoxysilane, isopropylisobutyldimethoxysilane, diisopentyldimethoxysilane, bis(2-ethylhexyl)dimethoxysilane, t-butylmethyldimethoxysilane, t-butylethyldimethoxysilane, dicyclopentyldimethoxysilane, dicyclohexyldimethoxysilane, cyclohexylcyclopentyldimethoxysilane, cyclohexylmethyldimethoxysilane, tetraethoxysilane, tetrabutoxysilane, bis(ethylamino)methylethylsilane, t-butylmethylbis(ethylamino)silane, bis(ethylamino)dicyclohexylsilane, dicyclopentylbis(ethylamino)silane, bis(methylamino)(methylcyclopentylamino)methylsilane, diethylaminotriethoxysilane, bis(cyclohexylamino)dimethoxysilane, bis(perhydroisoquinolino)dimethoxysilane, bis(perhydroquinolino)dimethoxysilane, and ethyl(isoquinolino)dimethoxysilane. Of them, preferred is at least one selected from phenyltrimethoxysilane, t-butylmethyldimethoxysilane, t-butylethyldimethoxysilane, diisopropyldimethoxysilane, isopropylisobutyldimethoxysilane, diisopentyldimethoxysilane, diphenyldimethoxysilane, dicyclopentyldimethoxysilane, cyclohexylmethyldimethoxysilane, tetramethoxysilane, tetraethoxysilane, t-butylmethylbis(ethylamino)silane, bis(ethylamino)dicyclohexylsilane, dicyclopentylbis(ethylamino)silane, bis(perhydroisoquinolino)dimethoxysilane and diethylaminotriethoxysilane.

Of the above organosilicon compound, more preferred is at least one selected from phenyltrimethoxysilane, t-butylmethyldimethoxysilane, t-butylethyldimethoxysilane, diisopropyldimethoxysilane, isopropylisobutyldimethoxysilane, diisopentyldimethoxysilane, diphenyldimethoxysilane, dicyclopentyldimethoxysilane, cyclohexylmethyldimethoxysilane, tetramethoxysilane, tetraethoxysilane, t-butylmethylbis(ethylamino)silane, bis(ethylamino)dicyclohexylsilane, dicyclopentylbis(ethylamino)silane, bis(perhydroisoquinolino)dimethoxysilane and diethylaminotriethoxysilane.

Examples of (III) external electron-donating compounds described above also include at least one selected from diether compounds (1,3-diether compounds) represented by the following general formula (6):

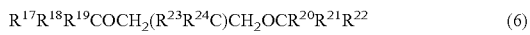

$R^{17}R^{18}R^{19}COCH_2(R^{23}R^{24}C)CH_2OCR^{20}R^{21}R^{22}$ (6)

wherein $R^{17}$ to $R^{22}$ are each any of a hydrogen atom, a linear alkyl group having 1 to 6 carbon atoms, a branched alkyl group having 3 to 6 carbon atoms, a cycloalkyl group having 3 to 6 carbon atoms, and a phenyl group, and may be the same or different from each other, and $R^{23}$ and $R^{24}$ are each any of a hydrogen atom, a linear alkyl group having 1 to 6 carbon atoms, a branched alkyl group having 3 to 6 carbon atoms, a cycloalkyl group having 3 to 6 carbon atoms, and a phenyl group, and may be the same or different from each other and may be bonded to each other to form a ring.

At least one selected from 2-isopropyl-2-isobutyl-1,3-dimethoxypropane, 2,2-diisobutyl-1,3-dimethoxypropane, 2-isopropyl-2-isopentyl-1,3-dimethoxypropane, 2,2-dicyclohexyl-1,3-dimethoxypropane, 2,2-bis(cyclohexylmethyl) 1,3-dimethoxypropane and 9,9-bis(methoxymethyl)fluorene is preferred, and at least one selected from 2-isopropyl-2-isobutyl-1,3-dimethoxypropane, 2-isopropyl-2-isopentyl-1, 3-dimethoxypropane and 9,9-bis(methoxymethyl)fluorene is more preferred as the diether compound represented by the above general formula (6).

In the catalyst for olefin polymerization according to the present invention, (III) external electron-donating compound is preferably at least one selected from the organosilicon compounds represented by the above general formula (4), the organosilicon compounds represented by the above general formula (5) and the diether compounds represented by the above general formula (6).

The catalyst for olefin polymerization according to the present invention contains (I) the solid catalyst component for olefin polymerization according to the present invention, (II) the organoaluminum compound represented by the general formula (3) and (III) an external electron-donating compound. In other words, the catalyst for olefin polymerization according to the present invention is a contact product thereof.

The catalyst for olefin polymerization according to the present invention may be prepared by contacting (I) the solid catalyst component for olefin polymerization according to the present invention, (II) the organoaluminum compound represented by the general formula (3) and (III) an external electron-donating compound in the absence of olefin, or in the presence of olefin (in a polymerization system) as described later.

The content ratio of the respective components in the catalyst for olefin polymerization according to the present invention is optional and not particularly limited as long as it does not affect the advantages of the present invention. The catalyst for olefin polymerization according to the present invention contains preferably 1 to 2,000 mol, more preferably 50 to 1,000 mol of (II) the above organoaluminum compound per mol of a titanium atom in (I) the above solid catalyst component for olefin polymerization. The catalyst for olefin polymerization according to the present invention contains preferably 0.002 to 10 mol, more preferably 0.01 to 2 mol, and further preferably 0.01 to 0.5 mol of (III) the above external electron-donating compound per mol of (II) the above organoaluminum compound.

The present invention provides a solid catalyst component for olefin polymerization comprising an electron-donating compound other than a phthalate, the solid catalyst component being equal in the olefin-polymerizing activity and in the primary physical properties of the resulting polymer such as stereoregularity and molecular weight distribution to those with use of a phthalate as an electron-donating compound.

Next, the method for producing an olefin polymer according to the present invention will be described.

The method for producing an olefin polymer according to the present invention polymerizes olefin in the presence of the catalyst for olefin polymerization according to the present invention.

In the method for producing an olefin polymer according to the present invention, the polymerization of olefin may be homopolymerization or copolymerization.

In the method for producing an olefin polymer according to the present invention, examples of an olefin to be polymerized include at least one selected from ethylene, propylene, 1-butene, 1-pentene, 4-methyl-1-pentene and vinylcyclohexane. Of them, at least one selected from ethylene, propylene and 1-butene is preferred, and propylene is more preferred.

When propylene is used as the olefin, propylene may be homopolymerized, or copolymerized with other olefins.

Examples of olefins to be copolymerized with propylene include at least one selected from ethylene, 1-butene, 1-pentene, 4-methyl-1-pentene and vinylcyclohexane.

When the catalyst for olefin polymerization according to the present invention is prepared in the presence of olefin (in a polymerization system), the ratio of the amount to be used of the components is optional and not particularly limited as long as it does not affect the advantages of the present invention. Preferably 1 to 2,000 mol, more preferably 50 to 1,000 mol of (II) the organoaluminum compound described above is contacted with (I) the solid catalyst component for olefin polymerization described above per mol of a titanium atom in (I) the solid catalyst component. Furthermore, preferably 0.002 to 10 mol, more preferably 0.01 to 2 mol, and further preferably 0.01 to 0.5 mol of (III) the external electron-donating compound described above is contacted with 1 mol of (II) the organoaluminum compound.

The order of contact of the respective components constituting the above catalyst for olefin polymerization is optional. It is preferable that (II) the organoaluminum compound is first introduced into the polymerization system, then (III) the external electron-donating compound is introduced thereinto to be contacted therewith, and then (I) the solid catalyst component for olefin polymerization is introduced thereinto to be contacted therewith.

The method for producing an olefin polymer according to the present invention may be performed in the presence or absence of an organic solvent.

Furthermore, olefin monomers such as propylene may be used in the form of gas or liquid. The polymerization temperature is preferably 200° C. or less, more preferably 100° C. or less. The polymerization pressure is preferably 10 MPa or less, and more preferably 5 MPa or less. Furthermore, either continuous polymerization or batch polymerization may be used for the polymerization of olefin. The reaction of polymerization may be in a single stage or two or more stages.

Furthermore, for the polymerization of olefin using the catalyst for olefin polymerization according to the present invention (also referred to as main polymerization), preliminary polymerization is preferably carried out before the main polymerization in order to further improve the catalytic activity, stereoregularity and properties of particles of the resulting polymer. Monomers such as olefins similar to those used in the main polymerization and styrene may be used in the preliminary polymerization.

In the preliminary polymerization, the order of contact of the respective components constituting the above catalyst for olefin polymerization and monomers (olefins) is optional. It is preferable that (II) the organoaluminum compound is first introduced into a preliminary polymerization system whose atmosphere is inert gas or olefin gas, then (I) the solid catalyst component for olefin polymerization according to the present invention is introduced thereinto to be contacted therewith, and then an olefin such as propylene alone or a mixture of an olefin such as propylene and one or more other olefins is contacted therewith.

In the above preliminary polymerization, if (III) an external electron-donating compound is also introduced into the preliminary polymerization system, it is preferable that (II) the organoaluminum compound is first introduced into a preliminary polymerization system whose atmosphere is inert gas or olefin gas, then (III) the external electron-donating compound is introduced thereinto to be contacted therewith, and (I) the solid catalyst component for olefin polymerization according to the present invention is further contacted therewith, and thereafter an olefin such as propylene alone or a mixture of an olefin such as propylene and one or more other olefins is contacted therewith.

When a propylene block copolymer is produced by the method for producing an olefin polymer according to the present invention, multi-stage polymerization including two or more stages is employed. It is preferable that propylene is polymerized in the presence of the catalyst for olefin polymerization according to the present invention in the first stage and ethylene and propylene are then copolymerized in the second stage. The second or later stages of polymerization may be carried out in the coexistence of propylene and α-olefin other than propylene, or in the presence of α-olefin other than propylene alone.

Examples of α-olefin other than propylene described above include at least one selected from ethylene, 1-butene, 4-methyl-1-pentene, vinylcyclohexane, 1-hexene and 1-octene.

In a specific example, propylene is homopolymerized in the first stage while adjusting temperature and time so that the proportion of the polypropylene block constituting the resulting copolymer is 20 to 80 mass %, and ethylene (or another α-olefin) and propylene are then introduced thereinto to perform polymerization in the second stage so that the proportion of the rubber portion such as ethylene-propylene rubber (EPR) constituting the resulting copolymer is 20 to 80 mass %. The polymerization temperature is preferably 200° C. or less, more preferably 100° C. or less in both the first and second stages. The polymerization pressure is preferably 10 MPa or less, and more preferably 5 MPa or less in both. The polymerization time (residence time) is usually 1 minute to 5 hours in total in both multi-stage polymerization and continuous polymerization.

In the method for producing an olefin polymer according to the present invention, processes of polymerization include a slurry polymerization process using a solvent of an inert hydrocarbon compound such as cyclohexane and heptane, a bulk polymerization process using a solvent such as liquid propylene, and a gas phase polymerization process in which substantially no solvent is used. The bulk polymerization process and the gas phase polymerization process are preferred.

The present invention provides a method for producing an olefin polymer by using a solid catalyst component for olefin polymerization comprising an electron-donating compound other than a phthalate, the solid catalyst component being equal in the primary physical properties of the resulting polymer such as stereoregularity and molecular weight distribution to those with use of a phthalate as an electron-donating compound.

EXAMPLES

Next, the present invention will be described in more detail by means of Examples, but these Examples are for illustration only and do not limit the present invention.

Example 1

1. Synthesis of Solid Catalyst Component

A flask with an inner volume of 500 ml equipped with a stirrer thoroughly purged with nitrogen gas was charged with 10 g (87.4 mmol) of diethoxy magnesium, 55 ml of toluene, 30 ml of titanium tetrachloride, 9.1 mmol (1.8 g) of ethyl 3-ethoxy-2-t-butylpropionate and 4.0 mmol (1.0 g) of diethyl benzylidenemalonate. The temperature was increased to 100° C. and the mixture was reacted for 90 minutes with the temperature kept at 100° C. After completion of the reaction, the reaction product was washed with 75 ml of toluene at 100° C. for 4 times. Subsequently, 100 ml of a 10% by volume titanium tetrachloride solution in toluene was added thereto, and the temperature was increased to 100° C. and the mixture was stirred for 15 minutes to perform reaction. After completion of the reaction, the reaction product was washed with toluene at 100° C. once. This procedure was performed twice more and then the resultant was washed with 75 ml of n-heptane at 40° C. for 6 times to give a solid catalyst component.

Solid in the solid catalyst component was separated from liquid, and the content of titanium, the content of ethyl 3-ethoxy-2-t-butylpropionate (corresponding to ester compound (A)), and the content of diethyl benzylidenemalonate (corresponding to diester compound (B)) in the resulting solid component were measured. As a result, the content was 2.7 mass %, 10.0 mass %, and 2.6 mass %, respectively. Furthermore, the content ratio calculated by (content (mass %) of ester compound (A)/content (mass %) of diester compound (B)) was 3.9.

The content of titanium, the content of ethyl 3-ethoxy-2-t-butylpropionate and the content of diethyl benzylidenemalonate in the solid component were measured as follows.
<Content of Titanium in Solid Component>

The content of titanium in the solid component was measured by the method described in JIS M 8301.
<Content of Electron-Donating Compound (Ester Compound (A), Diester Compound (B)) in Solid Component>

The content of the electron donor was determined by the measurement using gas chromatography (GC-14B made by Shimadzu Corporation) in the following condition. The number of moles of the respective components was determined from the results of measurement of the gas chromatography using a calibration curve which had been previously prepared by measurement at a known concentration.
(Conditions of Measurement)
    Column: packed column (ϕ 2.6×2.1 m, Silicone SE-30 10%, Chromosorb WAW DMCS 80/100 available from GL Sciences)
    Detector: FID (Flame Ionization Detector)
    Carrier gas: helium, flow rate 40 ml/minute
    Measurement temperature: vaporizing chamber 280° C., column 225° C., detector 280° C.

2. Preparation of Polymerization Catalyst and Polymerization

An autoclave with an inner volume of 2.0 liter equipped with a stirrer completely purged with nitrogen gas was charged with 1.32 mmol of triethylaluminum, 0.13 mmol of cyclohexylmethyldimethoxysilane (CMDMS) and 0.0026 mmol in terms of a titanium atom of the solid catalyst component to form a polymerization catalyst. Subsequently, 1.5 liter of hydrogen gas and 1.4 liter of liquid propylene were introduced thereinto to perform preliminary polymerization at 20° C. for 5 minutes, and then the temperature was increased and polymerization reaction was performed at 70° C. for 1 hour. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured by the following methods. The results are shown in Table 1.
<Polymerization Activity Per g of Solid Catalyst Component>

The polymerization activity per g of the solid catalyst component was determined by the following equation.

Polymerization activity (g-pp/g-catalyst)=mass of polymer (g)/mass of solid catalyst component (g)

<Xylene Soluble Component (XS) of Polymer>

A flask equipped with a stirrer was charged with 4.0 g of polymer (polypropylene) and 200 ml of p-xylene. The polymer was dissolved in p-xylene over 2 hours while keeping the temperature of p-xylene in the flask at its boiling point (137 to 138° C.) by adjusting the outside temperature at the boiling point (about 150° C.) or more. Subsequently, the solution was cooled to 23° C. over 1 hour, and insoluble components and soluble components were separated by filtration. The solution of soluble components was collected and p-xylene was evaporated by heating and drying under reduced pressure. The resulting residue was defined as a xylene soluble component (XS), and the mass was calculated as a value (mass %) relative to the mass of the polymer (polypropylene).
<Melt Flow Rate (MFR) of Polymer>

The melt flow rate (MFR), which is a measure of the ability of polymer melt to flow, was measured in accordance with ASTM D 1238, JIS K 7210.
<Molecular Weight Distribution of Polymer>

The molecular weight distribution of the polymer was evaluated by the ratio Mw/Mn, i.e., the ratio between weight average molecular weight Mw and number average molecular weight Mn, which was determined by the measurement using gel permeation chromatography (GPC) (GPCV2000 mad by Waters) in the following condition.
    Solvent: o-dichlorobenzene (ODCB)
    Temperature: 140° C. (SEC)
    Column: Shodex GPC UT-806M
    Concentration of sample: 1 g/liter-ODCB (50 mg/50 ml-ODCB)
    Injection volume: 0.5 ml
    Flow rate: 1.0 ml/min Example 2

Polymerization was carried out in the same manner as in Example 1 except for using 0.13 mmol of dicyclopentyldimethoxysilane (DCPDMS) instead of 0.13 mmol of cyclohexylmethyldimethoxysilane (CMDMS) in Example 1. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 3

A solid catalyst component was prepared in the same manner as in Example 1 except for using 6.8 mmol of ethyl 3-ethoxy-2-t-butylpropionate instead of 9.1 mmol thereof and 6.3 mmol of diethyl benzylidenemalonate instead of 4.0 mmol thereof in "1. Synthesis of solid catalyst component" in Example 1.

The content of titanium, the content of ethyl 3-ethoxy-2-t-butylpropionate (corresponding to ester compound (A)), and the content of diethyl benzylidenemalonate (corresponding to diester compound (B)) in the resulting solid catalyst component were measured. As a result, the content was 2.9 mass %, 7.7 mass % and 3.1 mass %, respectively. Furthermore, the content ratio calculated by (content (mass %) of ester compound (A)/content (mass %) of diester compound (B)) was 2.5.

Subsequently, a polymerization catalyst was prepared and polymerization was performed in the same manner as in "2. Preparation of polymerization catalyst and polymerization" in Example 1 except for using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 4

Polymerization was carried out in the same manner as in Example 3 except for using 0.13 mmol of dicyclopentyldimethoxysilane (DCPDMS) instead of 0.13 mmol of cyclohexylmethyldimethoxysilane (CMDMS) in Example 3. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 5

A solid catalyst component was prepared using 9.1 mmol (1.7 g) of ethyl 3-ethoxy-2-isopropylpropionate instead of 9.1 mmol (1.8 g) of ethyl 3-ethoxy-2-t-butylpropionate in "1. Synthesis of solid catalyst component" in Example 1. The content of titanium, the content of ethyl 3-ethoxy-2-isopropylpropionate (corresponding to ester compound (A)), and the content of diethyl benzylidenemalonate (corresponding to diester compound (B)) in the resulting solid catalyst component were measured. As a result, the content was 3.0 mass %, 9.0 mass % and 3.5 mass %, respectively. Furthermore, the content ratio calculated by (content (mass %) of ester compound (A)/content (mass %) of diester compound (B)) was 2.6.

Subsequently, polymerization was carried out in the same manner as in Example 1 except for using the above solid catalyst component and using 0.13 mmol of dicyclopentyldimethoxysilane (DCPDMS) instead of 0.13 mmol of cyclohexylmethyldimethoxysilane (CMDMS). The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 6

A solid catalyst component was prepared using 9.1 mmol (2.1 g) of diethyl 1-ethyl-3-methylbutylidenemalonate instead of 9.1 mmol (1.8 g) of diethyl benzylidenemalonate in "1. Synthesis of solid catalyst component" in Example 1.

The content of titanium, the content of ethyl 3-ethoxy-2-t-butylpropionate (corresponding to ester compound (A)), and the content of diethyl 1-ethyl-3-methylbutylidenemalonate (corresponding to diester compound (B)) in the resulting solid catalyst component were measured. As a result, the content was 2.9 mass %, 10.0 mass % and 2.1 mass %, respectively. Furthermore, the content ratio calculated by (content (mass %) of ester compound (A)/content (mass %) of diester compound (B)) was 4.8.

Subsequently, a polymerization catalyst was prepared and polymerization was performed in the same manner as in "2. Preparation of polymerization catalyst and polymerization" in Example 1 except for using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 7

Polymerization was carried out in the same manner as in Example 3 except for using 0.13 mmol of diethylaminotriethoxysilane (DEATES) instead of 0.13 mmol of cyclohexylmethyldimethoxysilane (CMDMS) in Example 3. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 8

Polymerization was carried out in the same manner as in Example 3 except for using 0.13 mmol of 9,9-bis(methoxymethyl)fluorene (BMMF) instead of 0.13 mmol of cyclohexylmethyldimethoxysilane (CMDMS) in Example 3. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 9

A solid catalyst component was prepared in the same manner as in Example 1 except for using 11.8 mmol (2.4 g) of ethyl 3-ethoxy-2-t-butylpropionate instead of 9.1 mmol (1.8 g) thereof and 1.3 mmol (0.3 g) of diethyl benzylidenemalonate instead of 4.0 mmol (1.0 g) thereof in "1. Synthesis of solid catalyst component" in Example 1.

The content of titanium, the content of ethyl 3-ethoxy-2-isopropylpropionate (corresponding to ester compound (A)), and the content of diethyl benzylidenemalonate (corresponding to diester compound (B)) in the resulting solid catalyst component were measured. As a result, the content was 2.9 mass %, 11.2 mass % and 0.5 mass %, respectively. Furthermore, the content ratio calculated by (content (mass %) of ester compound (A)/content (mass %) of diester compound (B)) was 22.4.

Subsequently, polymerization was carried out in the same manner as in Example 1 using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 10

A solid catalyst component was prepared in the same manner as in Example 1 except for using 1.3 mmol (0.3 g) of ethyl 3-ethoxy-2-t-butylpropionate instead of 9.1 mmol (1.8 g) thereof and 11.8 mmol (2.9 g) of diethyl benzylidenemalonate instead of 4.0 mmol (1.0 g) thereof in "1. Synthesis of solid catalyst component" in Example 1.

The content of titanium, the content of ethyl 3-ethoxy-2-isopropylpropionate (corresponding to ester compound (A)), and the content of diethyl benzylidenemalonate (corresponding to diester compound (B)) in the resulting solid catalyst component were measured. As a result, the content was 2.7 mass %, 0.8 mass % and 8.2 mass %, respectively. Furthermore, the content ratio calculated by (content (mass %) of ester compound (A)/content (mass %) of diester compound (B)) was 0.1.

Subsequently, polymerization was carried out in the same manner as in Example 1 using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Example 11

A solid catalyst component was prepared in the same manner as in Example 1 except for using 14.8 mmol (3.0 g) of ethyl 3-ethoxy-2-t-butylpropionate instead of 9.1 mmol (1.8 g) thereof and 0.9 mmol (0.2 g) of diethyl benzylidenemalonate instead of 4.0 mmol (1.0 g) thereof in "1. Synthesis of solid catalyst component" in Example 1.

The content of titanium, the content of ethyl 3-ethoxy-2-isopropylpropionate (corresponding to ester compound (A)), and the content of diethyl benzylidenemalonate (corresponding to diester compound (B)) in the resulting solid catalyst component were measured. As a result, the content was 2.5 mass %, 13.5 mass % and 0.3 mass %, respectively. Furthermore, the content ratio of ester compound (A) calculated by (content (mass %) of ester compound (A)/content (mass %) of diester compound (B)) was 45.0.

Subsequently, polymerization was carried out in the same manner as in Example 1 using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Comparative Example 1

A solid catalyst component was prepared in the same manner as in Example 1 except for not adding ethyl 3-ethoxy-2-t-butylpropionate and adding only 13.1 mmol (3.2 g) of diethyl benzylidenemalonate in "1. Synthesis of solid catalyst component" in Example 1.

The content of titanium and the content of diethyl benzylidenemalonate (corresponding to diester compound (B)) in the resulting solid catalyst component were measured. As a result, the content was 2.6 mass % and 10.8 mass %, respectively. Furthermore, the content ratio calculated by (content (mass %) of ester compound (A)/content (mass %) of diester compound (B)) was 0.

Subsequently, polymerization was carried out in the same manner as in Example 1 using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Comparative Example 2

Polymerization was carried out in the same manner as in Example 1 except for using the solid catalyst component prepared in Comparative Example 1 and using 0.13 mmol of dicyclopentyldimethoxysilane (DCPDMS) instead of 0.13 mmol of cyclohexylmethyldimethoxysilane (CMDMS).

The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Comparative Example 3

A solid catalyst component was prepared in the same manner as in Example 1 except for not adding diethyl benzylidenemalonate and adding only 13.1 mmol (2.6 g) of ethyl 3-ethoxy-2-t-butylpropionate in "1. Synthesis of solid catalyst component" in Example 1.

The content of titanium and the content of ethyl 3-ethoxy-2-t-butylpropionate (corresponding to diester compound (A)) in the resulting solid catalyst component were measured. As a result, the content was 2.7 mass % and 14.4 mass %, respectively.

Subsequently, polymerization was carried out in the same manner as in Example 1 using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Comparative Example 4

Polymerization was carried out in the same manner as in Example 1 except for using the solid catalyst component prepared in Comparative Example 3 and using 0.13 mmol of dicyclopentyldimethoxysilane (DCPDMS) instead of 0.13 mmol of cyclohexylmethyldimethoxysilane (CMDMS).

The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Reference Example 1

A solid catalyst component was prepared in the same manner as in Example 1 except for adding 13.1 mmol (3.6 g) of di-n-butyl phthalate instead of ethyl 3-ethoxy-2-t-butylpropionate and diethyl benzylidenemalonate in "1. Synthesis of solid catalyst component" in Example 1.

The content of titanium and the content of di-n-butyl phthalate in the resulting solid catalyst component were measured. As a result, the content was 3.6 mass % and 11.3 mass %, respectively.

Subsequently, polymerization was carried out in the same manner as in Example 1 using the above solid catalyst component. The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

Reference Example 2

Polymerization was carried out in the same manner as in Example 1 except for using the solid catalyst component prepared in Comparative Example 1 and using 0.13 mmol of dicyclopentyldimethoxysilane (DCPDMS) instead of 0.13 mmol of cyclohexylmethyldimethoxysilane (CMDMS).

The polymerization activity per g of the solid catalyst component, the proportion of p-xylene soluble components (XS) in the resulting polymer, the melt flow rate (MFR) of the resulting polymer, and the molecular weight distribution (Mw/Mn) of the polymer in this case were measured in the same manner as in Example 1. The results are shown in Table 1.

TABLE 1

| Test Example | Ester (A) content (wt %)/ diester (B) content (wt %)* | Polymerization activity (g-pp/g-catalyst) | XS (mass %) | MFR (g/10 minute) | Mw/Mn |
|---|---|---|---|---|---|
| Example 1 | 3.9 (10.0/2.6) | 60,100 | 2.0 | 8.1 | 4.6 |
| Example 2 | 3.9 (10.0/2.6) | 56,600 | 1.3 | 3.3 | 5.3 |
| Example 3 | 2.5 (7.7/3.1) | 56,900 | 2.2 | 6.9 | 4.8 |
| Example 4 | 2.5 (7.7/3.1) | 53,600 | 1.4 | 2.8 | 5.4 |
| Example 5 | 2.6 (9.0/3.5) | 43,400 | 1.7 | 2.9 | 5.3 |
| Example 6 | 4.8 (10.0/2.1) | 54,300 | 1.6 | 3.3 | 4.2 |
| Example 7 | 2.5 (7.7/3.1) | 40,800 | 2.9 | 84 | 5.0 |
| Example 8 | 2.5 (7.7/3.1) | 42,100 | 2.2 | 35 | 4.1 |
| Example 9 | 22.4 (11.2/0.5) | 54,900 | 1.2 | 3.1 | 5.8 |
| Example 10 | 0.1 (0.8/8.2) | 56,600 | 2.0 | 2.6 | 5.5 |
| Example 11 | 45.0 (13.5/0.3) | 57,500 | 1.3 | 3.9 | 5.6 |
| Comparative Example 1 | 0 | 50,900 | 3.6 | 12 | 5.6 |
| Comparative Example 2 | 0 | 58,800 | 2.5 | 1.8 | 5.4 |
| Comparative Example 3 | — | 48,000 | 1.9 | 7.6 | 5.1 |
| Comparative Example 4 | — | 44,700 | 1.2 | 3.1 | 5.8 |
| Reference Example 1 | — | 58,900 | 2.2 | 7.3 | 5.1 |
| Reference Example 2 | — | 56,800 | 1.8 | 3.5 | 4.8 |

*Ester (A) content (wt %) means the content (mass %) of ester compound (A), and diester (B) content (wt %) means the content (mass %) of diester compound (B)

Table 1 shows that Example 1 to Example 11 used a solid catalyst component for olefin polymerization containing a magnesium atom, a titanium atom, a halogen atom, an ester compound (A) represented by the general formula (1) and a diester compound (B) represented by the general formula (2), wherein the content ratio represented by (content (mass %) of ester compound (A)/content (mass %) of diester compound (B)) was 0.05 to 50, and thus the olefin-polymerizing activity was equal to that in Reference Example 1 and Reference Example 2 in which a phthalate was used as an electron-donating compound, and the resulting polymer has primary physical properties such as stereoregularity and molecular weight distribution (Mw/Mn) equal to those in Reference Example 1 and Reference Example 2.

Table 1 also shows that since the solid catalyst components for olefin polymerization of Comparative Example 1 to Comparative Example 2 do not contain a predetermined amount of ester compound (A) together with diester compound (B), the resulting polymer has XS higher than that in Example 1 and Example 2 and stereoregularity and crystallinity inferior to those in Example 1 and Example 2.

Furthermore, Table 1 shows that since the solid catalyst components for olefin polymerization of Comparative Example 3 and Comparative Example 4 do not contain a predetermined amount of diester compound (B) together with ester compound (A), the resulting polymer has an olefin-polymerizing activity lower than that in Example 1 and Example 2.

INDUSTRIAL APPLICABILITY

The present invention provides a solid catalyst component for olefin polymerization comprising an electron-donating compound other than a phthalate, the solid catalyst component being equal in the olefin-polymerizing activity and in the primary physical properties of the resulting polymer such as stereoregularity and molecular weight distribution to those with use of a phthalate as an electron-donating compound. The present invention also provides a catalyst for olefin polymerization and a method of polymerization of olefin using the solid catalyst component for olefin polymerization.

The invention claimed is:

1. A solid catalyst component for olefin polymerization comprising a magnesium atom, a titanium atom, a halogen atom, an ester compound (A) represented by the following general formula (1):

$$R^1-O-C(=O)-CR^2R^3-CR^4R^5-O-R^6 \quad (1)$$

wherein $R^1$ and $R^6$ are each a hydrocarbon group having 1 to 24 carbon atoms and may be the same or different from each other, and $R^2$ to $R^5$ are each a hydrogen atom or a hydrocarbon group having 1 to 24 carbon atoms and may be the same or different from each other, and a diester compound (B) represented by the following general formula (2):

$$R^7R^8C=C(COOR^9)(COOR^{10}) \quad (2)$$

wherein $R^7$ and $R^8$ are each a hydrogen atom or a hydrocarbon group having 1 to 24 carbon atoms and may be the same or different from each other, and $R^9$ and $R^{10}$ are each a hydrocarbon group having 1 to 24 carbon atoms and may be the same or different from each other, wherein a ratio represented by the following expression:

(content (mass %) of ester compound (A)/content (mass %) of diester compound (B))

is 0.05 to 50.

2. The solid catalyst component for olefin polymerization according to claim 1, wherein at least one of the hydrocarbon groups having 1 to 24 carbon atoms constituting the $R^1$ to $R^{10}$ is a group selected from a linear alkyl group having 1 to 24 carbon atoms, a branched alkyl group having 3 to 24 carbon atoms, a vinyl group, a linear alkenyl group having 3 to 20 carbon atoms, a branched alkenyl group having 3 to 20 carbon atoms, a cycloalkyl group having 3 to 20 carbon atoms, a cycloalkenyl group having 3 to 20 carbon atoms, and an aromatic hydrocarbon group having 6 to 20 carbon atoms.

3. The solid catalyst component for olefin polymerization according to claim 1, wherein at least one of the $R^3$ to $R^5$ is a hydrogen atom.

4. The solid catalyst component for olefin polymerization according to claim 1, wherein the $R^7$ is an aromatic hydrocarbon group.

5. A catalyst for olefin polymerization comprising:
(I) the solid catalyst component for olefin polymerization according to claim 1;
(II) an organoaluminum compound represented by the following general formula (3):

$$R^{11}{}_pAlQ_{3-p} \quad (3)$$

wherein $R^{11}$ is an alkyl group having 1 to 6 carbon atoms; Q is a hydrogen atom or a halogen atom; p is a real number satisfying $0<p\leq 3$; if a plurality of $R^{11}$ are present, $R^{11}$ may be the same or different from each other; and if a plurality of Q are present, Q may be the same or different from each other; and
(III) an external electron-donating compound.

6. The catalyst for olefin polymerization according to claim 5, wherein the external electron-donating compound (III) is one or more selected from:
an organosilicon compound represented by the following general formula (4):

$$R^{12}{}_qSi(OR^{13})_{4-q} \quad (4)$$

wherein $R^{12}$ is any of a linear alkyl group having 1 to 12 carbon atoms, a branched alkyl group having 3 to 12 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and q is an integer satisfying $0\leq q\leq 3$, and if q is 2 or more, a plurality of $R^{12}$ may be the same or different from each other; and $R^{13}$ represents any of a linear alkyl group having 1 to 4 carbon atoms, a branched alkyl group having 3 to 4 carbon atoms, a vinyl group, an alkenyl group having 3 to 12 carbon atoms, a cycloalkyl group having 3 to 12 carbon atoms, and an aromatic hydrocarbon group having 6 to 12 carbon atoms, and a plurality of $R^{13}$ may be the same or different from each other; and
an organosilicon compound represented by the following general formula (5):

$$(R^{14}R^{15}N)_sSiR^{16}{}_{4-s} \quad (5)$$

wherein $R^{14}$ and $R^{15}$ are each any of a hydrogen atom, a linear alkyl group having 1 to 12 carbon atoms, a branched alkyl group having 3 to 12 carbon atoms, a vinyl group, alkenyl group having 3 to 12 carbon atoms, a cycloalkyl group having 3 to 12 carbon atoms, and an aromatic hydrocarbon group having 6 to 12 carbon atoms, and $R^{14}$ and $R^{15}$ may be the same or different from each other and may be bonded to each other to form a ring; and
$R^{16}$ is any of a linear alkyl group having 1 to 12 carbon atoms or a branched alkyl group having 3 to 12 carbon atoms, a vinyl group, an alkenyl group having 3 to 12 carbon atoms, a cycloalkyl group having 3 to 12 carbon atoms, an aromatic hydrocarbon group having 6 to 12 carbon atoms, a linear alkoxy group having 1 to 12 carbon atoms or a branched alkoxy group having 3 to 12 carbon atoms, a vinyloxy group, an allyloxy group having 3 to 12 carbon atoms, and an aryloxy group having 6 to 12 carbon atoms, and if a plurality of $R^{16}$ are present, each $R^{16}$ may be the same or different from each other, and s is an integer of 1 to 3.

7. The catalyst for olefin polymerization according to claim 5, wherein the external electron-donating compound (III) is a diether compound represented by the following general formula (6);

$$R^{17}R^{18}R^{19}COCH_2(R^{23}R^{24}C)CH_2OCR^{20}R^{21}R^{22} \quad (6)$$

wherein $R^{17}$ to $R^{22}$ are each any of a hydrogen atom, a linear alkyl group having 1 to 6 carbon atoms, a branched alkyl group having 3 to 6 carbon atoms, a cycloalkyl group having 3 to 6 carbon atoms, and a phenyl group, and may be the same or different from each other; and $R^{23}$ and $R^{24}$ are each any of a hydrogen atom, a linear alkyl group having 1 to 6 carbon atoms, a branched alkyl group having 3 to 6 carbon atoms, a cycloalkyl group having 3 to 6 carbon atoms, and a phenyl group, and may be the same or different from each other and may also be bonded to each other to form a ring.

8. The catalyst for olefin polymerization according to claim 6, wherein the organosilicon compound is one or more selected from phenyltrimethoxysilane, t-butylmethyldimethoxysilane, t-butylethyldimethoxysilane, diisopropyldimethoxysilane, isopropylisobutyl dimethoxysilane, diisopentyldimethoxysilane, diphenyldimethoxysilane, dicyclopentyldimethoxysilane, cyclohexylmethyldimethoxysilane, tetramethoxysilane, tetraethoxysilane, t-butylmethylbis(ethylamino)silane, bis(ethylamino)dicyclohexylsilane, dicyclopentylbis(ethylamino)silane, bis(perhydroisoquinolino)dimethoxysilane, and diethylaminotriethoxysilane.

9. The catalyst for olefin polymerization according to claim 7, wherein the diether compound is one or more selected from 2-isopropyl-2-isobutyl-1,3-dimethoxypropane, 2-isopropyl-2-isopentyl-1,3-dimethoxypropane, and 9,9-bis(methoxymethyl)fluorene.

10. A method for producing an olefin polymer comprising polymerizing an olefin in the presence of the catalyst for olefin polymerization according to claim 5.

11. A method for producing an olefin polymer comprising polymerizing an olefin in the presence of the catalyst for olefin polymerization according to claim 6.

12. A method for producing an olefin polymer comprising polymerizing an olefin in the presence of the catalyst for olefin polymerization according to claim 7.

13. A method for producing an olefin polymer comprising polymerizing an olefin in the presence of the catalyst for olefin polymerization according to claim 8.

14. A method for producing an olefin polymer comprising polymerizing an olefin in the presence of the catalyst for olefin polymerization according to claim 9.

* * * * *